United States Patent
Gall et al.

(10) Patent No.: US 9,731,045 B2
(45) Date of Patent: Aug. 15, 2017

(54) SHAPE MEMORY POLYMER

(71) Applicant: The Regents of the University of Colorado, a Body Corporate, Denver, CO (US)

(72) Inventors: Kenneth Gall, Atlanta, GA (US); Christopher Yakacki, Denver, CO (US)

(73) Assignee: THE REGENTS OF THE UNIVERSITY OF COLORADO, Denver, CO (US)

( * ) Notice: Subject to any disclaimer, the term of this patent is extended or adjusted under 35 U.S.C. 154(b) by 0 days.

(21) Appl. No.: 14/148,617

(22) Filed: Jan. 6, 2014

(65) Prior Publication Data

US 2014/0121295 A1 May 1, 2014

Related U.S. Application Data

(60) Continuation of application No. 13/730,570, filed on Dec. 28, 2012, which is a division of application No.
(Continued)

(51) Int. Cl.
*A61L 27/16* (2006.01)
*A61B 17/04* (2006.01)
(Continued)

(52) U.S. Cl.
CPC .......... *A61L 27/16* (2013.01); *A61B 17/0401* (2013.01); *A61F 2/0811* (2013.01);
(Continued)

(58) Field of Classification Search
CPC .. A61B 2017/00871; A61B 2017/0448; A61L 27/14; A61L 27/50; A61L 2400/16;
(Continued)

(56) References Cited

U.S. PATENT DOCUMENTS 4,253,200 A 3/1981 Kelman
4,494,954 A 1/1985 Suminoe et al.
(Continued)

FOREIGN PATENT DOCUMENTS

CA 2527976 12/2004
EP 0336318 A2 10/1989
(Continued)

OTHER PUBLICATIONS

Cambridge Journals: MRS Table of Contents for vol. 855 (2004). MRS Online Processings Library. REtrieved online [Jun. 26, 2014]. Retrieved from internt <URL:http://journals.cambridge.org/action/displayIssue?jid=OPL&volumeId=855&seriesId=0&issueId=-1>.*
(Continued)

*Primary Examiner* — Sanza McClendon
(74) *Attorney, Agent, or Firm* — Abbott Medical Optics Inc.

(57) ABSTRACT

A polymer is composed of a linear chain acrylate and a multi-functional acrylate cross-linker. The polymerized composition exhibits a transition at a temperature between about 34° C. and about 50° C. The polymerized composition exhibits shape memory effects. In one embodiment, the linear chain is tert-butyl acrylate and the crosslinker is polyethylene glycol dimethacrylate. The resultant shape memory polymers may be used in medical devices to provide devices with different shapes for pre and post implantation.

18 Claims, 20 Drawing Sheets

Related U.S. Application Data

10/598,080, filed as application No. PCT/US2006/012934 on Apr. 3, 2006, now abandoned.

(60) Provisional application No. 60/667,876, filed on Apr. 1, 2005.

(51) Int. Cl.
   *A61F 2/08* (2006.01)
   *A61L 27/50* (2006.01)
   *A61B 17/00* (2006.01)

(52) U.S. Cl.
   CPC ..... *A61L 27/50* (2013.01); *A61B 2017/00871* (2013.01); *A61B 2017/0448* (2013.01); *A61F 2002/0835* (2013.01); *A61F 2002/0858* (2013.01); *A61F 2002/0864* (2013.01); *A61F 2002/0882* (2013.01); *A61F 2002/0888* (2013.01); *A61F 2210/0014* (2013.01); *A61L 2400/16* (2013.01); *A61L 2430/02* (2013.01)

(58) Field of Classification Search
   CPC ............. A61L 2403/02; A61L 2430/02; A61F 2/0881; A61F 2/0811; A61F 2002/0835; A61F 2002/0858; A61F 2002/0864; A61F 2002/0882; A61F 2002/0888; A61F 2210/0014
   USPC ......... 522/13, 114, 120, 121, 150, 153, 178, 522/182; 523/105, 113
   See application file for complete search history.

(56) References Cited

U.S. PATENT DOCUMENTS

| | | |
|---|---|---|
| 4,528,311 A | 7/1985 | Beard et al. |
| 4,573,998 A | 3/1986 | Mazzocco |
| 4,594,401 A | 6/1986 | Takahashi et al. |
| 4,606,336 A | 8/1986 | Zeluff |
| 4,731,079 A | 3/1988 | Stoy |
| 4,820,782 A | 4/1989 | Ueno |
| 4,889,664 A | 12/1989 | Kindt-Larsen et al. |
| 4,950,258 A | 8/1990 | Kawai et al. |
| 4,955,580 A | 9/1990 | Seden et al. |
| 4,994,069 A | 2/1991 | Ritchart et al. |
| 5,116,337 A | 5/1992 | Johnson |
| 5,163,952 A | 11/1992 | Froix |
| 5,192,303 A | 3/1993 | Gatturna et al. |
| 5,234,430 A | 8/1993 | Huebner |
| 5,258,020 A | 11/1993 | Froix |
| 5,331,073 A | 7/1994 | Weinschenk, III |
| 5,358,511 A | 10/1994 | Gatturna et al. |
| 5,391,168 A | 2/1995 | Sanders et al. |
| 5,395,374 A | 3/1995 | Miller et al. |
| 5,445,140 A | 8/1995 | Tovey |
| 5,450,842 A | 9/1995 | Tovey et al. |
| 5,505,735 A | 4/1996 | Li |
| 5,551,871 A | 9/1996 | Besselink et al. |
| 5,562,663 A | 10/1996 | Wisnewski et al. |
| 5,599,291 A | 2/1997 | Balbierz et al. |
| 5,601,557 A | 2/1997 | Hayhurst |
| 5,603,722 A | 2/1997 | Phan et al. |
| 5,609,608 A | 3/1997 | Benett et al. |
| 5,674,241 A | 10/1997 | Bley et al. |
| 5,674,242 A | 10/1997 | Phan et al. |
| 5,702,402 A | 12/1997 | Brady |
| 5,728,098 A | 3/1998 | Sherman et al. |
| 5,762,630 A | 6/1998 | Bley et al. |
| 5,765,682 A | 6/1998 | Bley et al. |
| 5,797,911 A | 8/1998 | Sherman et al. |
| 5,866,635 A | 2/1999 | Collins et al. |
| 5,879,382 A | 3/1999 | Boneau |
| 5,899,938 A | 5/1999 | Sklar et al. |
| 5,911,737 A | 6/1999 | Lee et al. |
| 5,928,237 A | 7/1999 | Farris et al. |
| 5,961,520 A | 10/1999 | Beck et al. |
| 5,964,744 A | 10/1999 | Balbierz et al. |
| 5,968,070 A | 10/1999 | Bley et al. |
| 5,976,187 A | 11/1999 | Richelsoph |
| 6,024,764 A | 2/2000 | Schroeppel |
| 6,053,944 A | 4/2000 | Tran et al. |
| 6,059,815 A | 5/2000 | Lee et al. |
| 6,077,268 A | 6/2000 | Farris et al. |
| 6,090,125 A | 7/2000 | Horton |
| 6,102,933 A | 8/2000 | Lee et al. |
| 6,160,084 A | 12/2000 | Langer et al. |
| 6,165,198 A | 12/2000 | McGurk et al. |
| 6,210,413 B1 | 4/2001 | Justis et al. |
| 6,235,028 B1 | 5/2001 | Brumfield et al. |
| 6,240,630 B1 | 6/2001 | Lee et al. |
| 6,241,691 B1 | 6/2001 | Ferrera et al. |
| 6,248,129 B1 | 6/2001 | Froix |
| 6,264,694 B1 | 7/2001 | Weiler |
| 6,281,262 B1 | 8/2001 | Shikinami |
| 6,293,949 B1 | 9/2001 | Justis et al. |
| 6,296,643 B1 | 10/2001 | Hopf et al. |
| 6,299,613 B1 | 10/2001 | Ogilvie et al. |
| 6,353,069 B1 | 3/2002 | Freeman et al. |
| 6,368,356 B1 | 4/2002 | Zhong et al. |
| 6,388,043 B1 | 5/2002 | Langer et al. |
| 6,500,204 B1 | 12/2002 | Igaki |
| 6,514,237 B1 | 2/2003 | Maseda |
| 6,514,257 B2 | 2/2003 | Dovesi et al. |
| 6,616,617 B1 | 9/2003 | Ferrera et al. |
| 6,620,195 B2 | 9/2003 | Goble et al. |
| 6,632,245 B2 | 10/2003 | Kim |
| 6,637,995 B1 | 10/2003 | White |
| 6,702,976 B2 | 3/2004 | Sokolowski |
| 6,712,810 B2 | 3/2004 | Harrington et al. |
| 6,720,402 B2 | 4/2004 | Langer et al. |
| 6,730,124 B2 | 5/2004 | Steiner |
| 6,740,094 B2 | 5/2004 | Maitland et al. |
| 6,746,461 B2 | 6/2004 | Fry |
| 6,780,899 B2 | 8/2004 | Liao et al. |
| 6,814,756 B1 | 11/2004 | Michelson |
| 6,887,266 B2 | 5/2005 | Williams et al. |
| 6,929,233 B2 | 8/2005 | Andino et al. |
| 6,935,743 B2 | 8/2005 | Shadduck |
| 7,115,691 B2 | 10/2006 | Alvarado et al. |
| 7,151,157 B2 | 12/2006 | Mather |
| 7,208,550 B2 | 4/2007 | Mather et al. |
| 7,217,744 B2 | 5/2007 | Lendlein et al. |
| 7,291,154 B2 | 11/2007 | Maitland et al. |
| 7,303,642 B2 | 12/2007 | Topolkaraev |
| 7,611,524 B1 | 11/2009 | Maitland et al. |
| 7,632,303 B1 | 12/2009 | Stalker et al. |
| 7,651,528 B2 | 1/2010 | Montgomery et al. |
| 7,699,893 B2 | 4/2010 | Donnelly et al. |
| 7,731,750 B2 | 6/2010 | Bojarski et al. |
| 7,794,476 B2 | 9/2010 | Wisnewski |
| 8,241,567 B2 | 8/2012 | Cai et al. |
| 8,377,120 B2 | 2/2013 | Lipshitz et al. |
| 8,685,089 B2 | 4/2014 | Kahook et al. |
| 2001/0018619 A1 | 8/2001 | Enzerink et al. |
| 2001/0041937 A1 | 11/2001 | Rieser et al. |
| 2002/0013586 A1 | 1/2002 | Justis et al. |
| 2002/0062547 A1 | 5/2002 | Chiodo et al. |
| 2002/0161371 A1 | 10/2002 | Bezemer et al. |
| 2002/0188298 A1 | 12/2002 | Chan |
| 2003/0055198 A1 | 3/2003 | Langer et al. |
| 2003/0066533 A1 | 4/2003 | Loy |
| 2003/0083735 A1 | 5/2003 | Denardo et al. |
| 2003/0147046 A1 | 8/2003 | Shadduck |
| 2003/0149470 A1 | 8/2003 | Alvarado et al. |
| 2003/0149480 A1 | 8/2003 | Shadduck |
| 2003/0191276 A1 | 10/2003 | Lendlein et al. |
| 2004/0014929 A1 | 1/2004 | Lendlein et al. |
| 2004/0024143 A1 | 2/2004 | Lendlein et al. |
| 2004/0030062 A1 | 2/2004 | Mather et al. |
| 2004/0068262 A1 | 4/2004 | Lemos et al. |
| 2004/0098110 A1 | 5/2004 | Williams et al. |
| 2004/0110285 A1 | 6/2004 | Lendlein et al. |
| 2004/0117955 A1 | 6/2004 | Barvosa-Carter et al. |
| 2004/0122174 A1 | 6/2004 | Mather et al. |

(56) References Cited

U.S. PATENT DOCUMENTS

| | | |
|---|---|---|
| 2004/0138678 A1 | 7/2004 | Brown |
| 2004/0215192 A1 | 10/2004 | Justis et al. |
| 2004/0260298 A1 | 12/2004 | Kaiser et al. |
| 2005/0033163 A1 | 2/2005 | Duchon et al. |
| 2005/0033295 A1 | 2/2005 | Wisnewski |
| 2005/0070905 A1 | 3/2005 | Donnelly et al. |
| 2005/0090822 A1 | 4/2005 | DiPoto |
| 2005/0203622 A1 | 9/2005 | Steiner et al. |
| 2005/0212630 A1 | 9/2005 | Buckley et al. |
| 2005/0228500 A1 | 10/2005 | Kim et al. |
| 2005/0244353 A1 | 11/2005 | Lendlein et al. |
| 2006/0009785 A1 | 1/2006 | Maitland et al. |
| 2006/0030933 A1 | 2/2006 | DeLegge et al. |
| 2006/0036045 A1 | 2/2006 | Wilson et al. |
| 2006/0041089 A1 | 2/2006 | Mather et al. |
| 2006/0095134 A1 | 5/2006 | Trieu et al. |
| 2006/0096044 A1 | 5/2006 | Miki et al. |
| 2006/0129232 A1 | 6/2006 | Decarlo et al. |
| 2006/0136057 A1 | 6/2006 | Brulez et al. |
| 2006/0142794 A1 | 6/2006 | Lendlein et al. |
| 2006/0155287 A1 | 7/2006 | Montgomery et al. |
| 2006/0206140 A1 | 9/2006 | Shaolian et al. |
| 2006/0213522 A1 | 9/2006 | Menchaca et al. |
| 2006/0270749 A1 | 11/2006 | Salamone et al. |
| 2007/0004863 A1 | 1/2007 | Mentak |
| 2007/0078515 A1 | 4/2007 | Brady |
| 2007/0141339 A1 | 6/2007 | Song et al. |
| 2007/0298068 A1 | 12/2007 | Badawi et al. |
| 2007/0299487 A1 | 12/2007 | Shadduck |
| 2008/0004692 A1 | 1/2008 | Henson et al. |
| 2008/0021166 A1* | 1/2008 | Tong et al. ............... 525/241 |
| 2008/0141736 A1 | 6/2008 | Jones et al. |
| 2008/0177303 A1 | 7/2008 | Anthamatten et al. |
| 2008/0228186 A1 | 9/2008 | Gall et al. |
| 2008/0236601 A1 | 10/2008 | Jacobus |
| 2008/0281405 A1 | 11/2008 | Williams et al. |
| 2009/0005777 A1 | 1/2009 | Houser et al. |
| 2009/0149617 A1 | 6/2009 | Gall et al. |
| 2009/0149952 A1 | 6/2009 | Shadduck |
| 2009/0222025 A1 | 9/2009 | Catanese, III et al. |
| 2009/0234449 A1 | 9/2009 | De Juan, Jr. et al. |
| 2009/0248141 A1* | 10/2009 | Shandas ............ A61B 17/12022 623/1.19 |
| 2010/0065975 A1 | 3/2010 | Chen |
| 2010/0119833 A1 | 5/2010 | Madsen et al. |
| 2010/0145445 A1 | 6/2010 | Aharoni et al. |
| 2011/0002464 A1 | 1/2011 | Lipshitz et al. |
| 2011/0144227 A1* | 6/2011 | Bowman ................ A61L 27/50 522/96 |
| 2012/0232648 A1 | 9/2012 | Kahook et al. |
| 2014/0172094 A1 | 6/2014 | Kahook et al. |
| 2014/0277439 A1 | 9/2014 | Hu et al. |

FOREIGN PATENT DOCUMENTS

| | | |
|---|---|---|
| EP | 0368274 | 5/1990 |
| EP | 0668055 | 8/1995 |
| EP | 1481640 | 12/2004 |
| EP | 1607048 | 12/2005 |
| EP | 2683819 A2 | 1/2014 |
| JP | H02142778 A | 5/1990 |
| JP | 2003145564 | 5/2003 |
| WO | WO92/13490 | 8/1992 |
| WO | WO96/11721 | 4/1996 |
| WO | WO2004/014217 | 2/2004 |
| WO | WO2004/110313 | 12/2004 |
| WO | 2006108114 A2 | 10/2006 |
| WO | 2007001407 A2 | 1/2007 |
| WO | WO2007/038429 | 4/2007 |
| WO | WO2007/089843 | 8/2007 |
| WO | WO2008/051254 | 5/2008 |
| WO | 2012040380 A1 | 3/2012 |
| WO | 2012122320 A2 | 9/2012 |
| WO | 2013040434 A1 | 3/2013 |
| WO | 2014085827 A1 | 6/2014 |
| WO | 2015038940 A1 | 3/2015 |

OTHER PUBLICATIONS

International Search Report and Written Opinion, PCT/US2006/015207 (Aug. 18, 2006).

International Search Report and Written Opinion, PCT/US2008/058249 (Jul. 22, 2008).

International Search Report and Written Opinion, PCT/US2008/071066 (Jul. 24, 2009).

Bellin et al., "Polymeric Triple-Shape Materials", 103 Proc. Nat'l Acad. Sci. U.S.A. (PNAS), 18043-18047 (2006).

Diani et al., "Finite Strain 3D Thermoviscoelastic Constitutive Model for Shape Memory Polymers", 42 Polymer Engineering and Science, 486-492 (2006).

El Feninat et al., "Shape Memory Materials for Biomedical Applications", Advanced Engineering Materials, 4, No. 3, pp. 91-104 (2007).

Franzesi, "Design of a Novel Anterior Cruciate Ligament Prosthesis", Massachusetts Institute of Technology Thesis (2006), http://hdl.handle.net/1721.1/36693.

Gall et al., "Thermomechanics of the Shape Memory Effect in Polymers for Biomedical Applications", Wiley InterScience, pp. 339-348 (2005).

Gall et al., "Shape-Memory Polymers for Microelectromechanical Systems", Journal of Microelectromechanical Systems, vol. 13, No. 3, pp. 472-483 (Jun. 2004).

Gall et al., "Shape Memory Polymer Nanocomposites", Acta Materialia 50, pp. 5115-5126 (2002).

Jeon et al., "Shape Memory and Nanostructure in Poly(Norbornyl-POSS) Copolymers", Polymers International 49, pp. 453-457 (2000).

Langer et al., "Designing Materials for Biology and Medicine", Nature, vol. 428, pp. 487-492 (Apr. 1, 2004).

Lendlein et al., "Shape Memory Polymers as Stimuli-Sensitive Implant Materials", 32 Clinical Hemorheology and Microcirculation, 105-116 (2005).

Lendlein et al., "Light-Induced Shape-Memory Polymers", Nature, vol. 434, pp. 879-882 (Apr. 14, 2005).

Lendlein et al., "AB-Polymer Networks Based on Oligo (Varepsilon-Caprolactone) Segments Showing Shape-Memory Properties", Proceedings of the National Academy of Sciences of the United States of America, vol. 98, No. 3, pp. 842-847 (Jan. 30, 2001).

Lin et al., "Study on Shape-Memory Behavior of Polyether-Based Polyurethanes. I. Influence of the Hard-Segment Content", Journal of Applied Polymer Science, vol. 69, pp. 1563-1574 (1998).

Lin et al., "Study on Shape-Memory Behavior of Polyether-Based Polyurethanes. II. Influence of the Soft-Segment Molecular Weight", Journal of Applied Polymer Science, vol. 69, pp. 1575-1586 (1998).

Liu et al., "Thermomechanical Recovery Couplings of Shape Memory Polymers: Uniaxial Experiments and Constitutive Modeling", International Journal of Plasticity, vol. 22, pp. 279-313 (2006).

Liu et al., "Thermomechanical Recovery Couplings of Shape Memory Polymers in Flexure", Smart Materials and Structures, vol. 12, pp. 947-954 (2003).

Liu et al., "Chemically Cross-Linked Polycyclooctene Jul. 28, 2008 Synthesis, Characterization and Shape Memory Behavior", Macromolecules, vol. 35, No. 27, pp. 9868-9874 (2002).

Maitland et al., "Photothermal Properties of Shape Memory Polymer Micro-Actuators for Treating Stroke", Lasers in Surgery and Medicine, vol. 30, pp. 1-11 (2002).

Metcalfe et al., "Cold Hibernated Elastic Memory Foams for Endovascular Interventions", Biomaterials, vol. 24, pp. 491-497 (2003).

Metzger et al., "Mechanical Properties of Mechanical Actuator for Treating Ischemic Stroke", Biomedical Microdevices, vol. 4, No. 2, pp. 89-96 (2002).

(56) References Cited

OTHER PUBLICATIONS

Rupp et al., "Resulting Tensile Forces in the Human Bone-Patellar Tendon-Bone Graft: Direct Force Measurement in Vitro, Arthroscopy", Journal of Arthroscopic and Related Surgery, vol. 15, No. 2, pp. 179-184 (Mar. 1999).
Smith, T., "Strength of Elastomers—A Perspective", Polymer Engineering and Science, vol. 17, No. 3, pp. 129-143 (Mar. 1977).
Smith, T., "Time and Temperature Dependence of the Ultimate Properties of an SBR Rubber at Constant Elongations", Journal of Applied Physics, vol. 31, No. 11, pp. 1892-1898 (Nov. 1960).
Smith, T., "Ultimate Tensile Properties of Elastomers. I. Characterization by a Time and Temperature Independent Failure Envelope", Journal of Polymer Science, Part A, vol. 1, No. 12, pp. 3597-3616 (Dec. 1963).
Sokolowski et al., "Cold Hibernated Elastic Memory (CHEM) Self-Deployable Structures", SPIE 1999 International Symposium on Smart Structures and Materials (1999).
Sokolowski et al., "Medical Applications of Shape Memory Polymers", 2 Biomedical Materials, S23-S27 (2007).
Takahashi et al., "Structure and Properties of Shape-Memory Polyurethane Block Copolymers", Journal of Applied Polymer Science, vol. 60, pp. 1061-1069 (1996).
Tobushi et al., "Thermomechanical Constitutive Modeling in Shape Memory Polymer of Polyurethane Series", Journal of Intelligent Material Systems and Structures, vol. 8, pp. 711-718 (Aug. 1997).
Tobushi et al., "Thermomechanical Properties in a Thin Film of Shape Memory Polymer of Polyurethane Series", Smart Matter Structures, vol. 5, pp. 483-491 (1996).
Wache et al., "Development of a Polymer Stent with Shape Memory Effect as a Drug Delivery System", Journal of Materials Science: Materials in Medicine, vol. 14, pp. 109-112 (2003).
Zhu et al., "Shape-Memory Effects of Radiation Crosslinked Poly ($\varepsilon$-Capralactone -Caprolactone)" Journal of Applied Polymer Science, vol. 90, pp. 1589-1595 (2005).
Author Unknown, "0.018" and 0.035" Fibered Platinum Coils", Boston Scientific Corporation, 1 page (2010).
Author Unknown, "Brain Aneurysm Treatment", Boston Scientific Corporation, 2 pages (2010).
Author Unknown, "Development of Aneurysm Treatment using Laser-Deployed Shape Memory Polymer Foams", University of California, Davis, 3 pages (2002-2009).
Author Unknown, "Embolic Coils", International Neuro Products, 1 page (2010).
Author Unknown, "Enhanced Embolic Coils for the Treatment of Cerebral Aneurysms", Micrus Endovascular, 3 pages (2010).
Author Unknown, "ePAX", NeuroVasx, 1 page, date unknown.
Author Unknown, "HydroSoft", MicroVention Terumo, 2 pages (2010).
Author Unknown, "Matrix2 Detachable Coils", Boston Scientific Corporation, 8 pages, date unknown.
Author Unknown, "MicroPlex Coil System", MicroVention Terumo, 1 page (2010).
Author Unknown, "Neurovascular Intervention", Boston Scientific Corporation, 2 pages (2010).
Author Unknown, "HydroCoil", MicroVention Terumo, 2 pages (2010).
Author Unknown, "Trufill DCS Orbit Detachable Coil System", Codman & Shurtleff, Inc., 2 pages (2000-2010).
Author Unknown, "Shape Memory Therapeutics Receives Texas Emerging Technology Fund Award", Texas A&M University, 2 pages (2009).
Author Unknown, "VortX 18 and 35 Vascular Occlusion Coils", Boston Scientific Corporation, 2 pages (2010).
Denardo et al., "Shape Memory Polymer Foams for Cerebral Aneurysm Reparation: Effects of Plasma Sterilization on Physical Properties and Cytocompatibility", ActaBiomaterialia, pp. 1508-1518 (2009).
Hampikian et al., "Mechanical and Radiographic Properties of a Shape Memory Polymer Composite for Intracranial Aneurysm Coils", Materials, Science and Engineering, pp. 1373-1379 (2006).
Heaton, "A Shape Memory Polymer for Intracranial Aneurysm Coils: An Investigation of Mechanical and Radiographic Properties of a Tantalum-Filled Shape Memory Polymer Composite", Thesis Presented to Academic Faculty, Georgia Institute of Technology, 60 pages (Jul. 2004).
Maitland et al., "Design and Realization of Biomedical Devices Based on Shape Memory Polymers", Materials Research Society Website; www.mrs.org, (2009).
Maitland et al., "Photothermal Properties of Shape Memory Polymer Micro-Actuators for Treating Stroke", Lasers in Surgery and Medicine 30:1-11 (2002).
Maitland et al., "Prototype Laser-activated Shape Memory Polymer Foam Device for Embolic Treatment of Aneurysms", Journal of Biomedical Optics, V.12:3, 3 pages (May/Jun. 2007).
Metzger et al., "Mechanical Properties of Mechanical Actuator for Treating Ischemic Stroke", Biomedical Microdevices 4:2, pp. 89-96 (2002).
Small et al., "Biomedical Applications of Thermally Activated Shape Memory Polymers", Journal of Materials Chemistry, pp. 3356-3366 (2010).
Wilson et al., "Shape Memory Polymer Therapeutic Devices for Stroke", Smart Medical and Biomedical Sensor Technology III, 8 pages (2005).
Yakacki et al., "Optimizing the Thermomechanics of Shape-Memory Polymers for Biomedical Applications", Mater. Res. Soc. Symp. Proc. vol. 855E, Materials Research Society, 6 pages (Jan. 5, 2005).
Yakacki et al., "Thermomechanics of Shape-Memory Polymers for Biomedical Applications", presented at Symposium W—Mechanically Active Materials, Materials Research Society, Nov. 30-Dec. 1, 2004.
EP Application No. 07759877, Supplementary Search Report dated Feb. 7, 2011, 4 pages.
PCT Application No. PCT/US2007/06591, International Search Report dated Sep. 21, 2007, 2 pages.
Non-Final Office Action dated Dec. 27, 2010, U.S. Appl. No. 12/295,594, 16 pages.
Response to Non-Final Office Action dated Jun. 24, 2011, U.S. Appl. No. 12/295,594, 22 pages.
Non-Final Office Action dated Feb. 1, 2012, U.S. Appl. No. 12/295,594, 20 pages.
Response to Non-Final Office Action dated Jul. 26, 2012, U.S. Appl. No. 12/295,594, 22 pages.
Non-Final Office Action dated Oct. 18, 2012, U.S. Appl. No. 12/295,594, 20 pages.
Response to Non-Final Office Action dated Feb. 19, 2013, U.S. Appl. No. 12/295,594, 17 pages.
Non-Final Office Action dated May 9, 2013, U.S. Appl. No. 12/295,594, 17 pages.
Bellin I., et al., "Polymeric Triple-Shape Materials," Proceedings of the National Academy of Sciences, 2006, vol. 103 (48), pp. 18043-18047.
Diani., et al., "Finite Strain 3D Thermoviscoelastic Constitutive Model for Shape Memory Polymers," Polymer Engineering & Science, 2006, vol. 46 (4), pp. 486-492.
El Feninat, et al., "Shape Memory Materials for Biomedical Applications," Advanced Engineering Materials, 2002, vol. 4 (3), pp. 91-104.
Gall, et al., "Shape Memory Polymer Nanocomposites," Acta Materialia, 2002, vol. 50 (20), pp. 5115-5126.
Gall, et al., "Shape-Memory Polymers for Microelectromechanical Systems," Journal of Microelectromechanical Systems, 2004, vol. 13 (3), pp. 472-483.
Gall, et al., "Thermomechanics of the Shape Memory Effect in Polymers for Biomedical Applications," Journal of Biomedical Materials Research, 2005, vol. 73 (3), pp. 339-348.
International Search Report and Written Opinion for Application No. PCT/US2012/028150, dated Feb. 1, 2013, 10 pages.
International Search Report and Written Opinion for Application No. PCT/US2014/055459, dated Dec. 4, 2014, 12 pages.

(56) References Cited

OTHER PUBLICATIONS

Jeon., et al., "Shape Memory and Nanostructure in Poly(Norbornyl-Poss) Copolymers," Polymer International, 2000, vol. 49 (5), pp. 453-457.

Langer., et al., "Designing Materials for Biology and Medicine," Nature, 2004, vol. 428 (6982), pp. 487-492.

Lendlein.A., et al., "Ab-Polymer Networks Based on Oligo(Epsilon-Caprolactone) Segments Showing Shape-Memory Properties," Proceedings of the National Academy of Sciences, 2001, vol. 98 (3), pp. 842-847.

Lendlein.A., et al., "Biodegradable, Elastic Shape-Memory Polymers for Potential Biomedical Applications," Science, 2002, vol. 296 (5573), pp. 1673-1676.

Lendlein.A. et al., "Shape-Memory Polymers As Stimuli-Sensitive Implant Materials," Clinical Hemorheology and Microcirculation, 2005, vol. 32 (2), pp. 105-116.

Lendlein.A., et al., "Light-Induced Shape-Memory Polymers," Nature, 2005, vol. 434 (7035), pp. 879-882.

Lin. et al. "Study on Shape-Memory Behavior of Polyether-Based Polyurethanes. I. Influence of the Hard-Segment Content," Journal of Applied Polymer Science, 1998, vol. 69 (8), pp. 1563-1574.

Lin., et al. "Study on Shape-Memory Behavior of Polyether-Based Polyurethanes. Ii. Influence of Soft-Segment - Molecular Weight," Journal of Applied Polymer Science, 1998, vol. 69 (8), pp. 1575-1586.

Liu., et al., "Chemically Cross-Linked Polycyclooctene: Synthesis, Characterization, and Shape Memory Behavior," Macromolecules, 2002, vol. 35 (27), pp. 9868-9874.

Liu., et al. "Thermomechanical Recovery Couplings of Shape Memory Polymers in Flexure," Smart Materials and Structures, 2003, vol. 12 (6), pp. 947-954.

Liu., et al., "Thermomechanics of Shape Memory Polymers: Uniaxial Experiments and Constitutive Modeling," International Journal of Plasticity, 2006, vol. 22 (2), pp. 279-313.

Maitland., et al., "Photothermal Properties of Shape Memory Polymer Micro-Actuators for Treating Stroke," Lasers in Surgery and Medicine, 2002, vol. 30 (1), pp. 1-11.

Metcalfe., et al., "Cold Hibernated Elastic Memory Foams for Endovascular Interventions," Biomaterials, 2003, vol. 24 (3), pp. 491-497.

Metzger., et al., "Mechanical Properties of Mechanical Actuator for Treating Ischemic Stroke," Biomedical Microdevices, 2002, vol. 4 (2), pp. 89-96.

Rupp., et al. "Resulting Tensile Forces in the Human Bone-Patellar Tendon-Bone Graft: Direct Force Measurement in Vitro," Arthroscopy, 1999, vol. 15 (2), pp. 179-184.

Smith.T, "Time and Temperature Dependence of the Ultimate Properties of an Sbr Rubber At Constant Elongations," Journal of Applied Physics, 1960, vol. 31 (11), pp. 1892-1898.

Smith.T, "Strength of Elastomers," Polymer Engineering and Science, 1977, vol. 17 (3), pp. 129-143.

Smith.T, "Ultimate Tensile Properties of Elastomers. I. Characterization By a Time and Temperature Independent Failure Envelope," Journal of Polymer Science, 1963, vol. 1 (12), pp. 3597-3615.

Sokolowski., et al., "Medical Applications of Shape Memory Polymers," Biomedical Materials, 2007, vol. 2, pp. S23-S27.

Supplementary European Search Report for Application No. EP12755496, dated May 21, 2015, 7 pages.

Takahashi., et al., "Structure and Properties of Shape-Memory Polyurethane Block Copolymers," Journal of Applied Polymer Science, 1996, vol. 60, pp. 1061-1069.

Tobushi., et al., "Thermomechanical Constitutive Modeling in Shape Memory Polymer of Polyurethane Series," Journal of Intelligent Material Systems, 1997, vol. 8 (8), pp. 711-718.

Tobushi., et al., "Thermomechanical Properties in A Thin Film of Shape Memory Polymer of Polyurethane Series," Smart Materials and Structures, 1996, vol. 5 (4), pp. 483-491.

Wache., et al., "Development of A Polymer Stent With Shape Memory Effect As a Drug Delivery System," Journal of Materials Science, 2003, vol. 14 (2), pp. 109-112.

Yakacki C.M., et al., "Strong, Tailored, Biocompatible Shape-Memory Polymer Networks," Advanced Functional Materials, 2008, vol. 8 (16), pp. 2428-2435.

Zhu., et al., "Shape-Memory Effects of Radiation Crosslinked Poly(E-Caprolactone)," Journal of Applied Polymer Science, 2003, vol. 90 (6), pp. 1589-1595.

\* cited by examiner

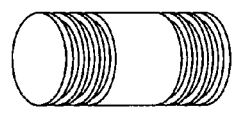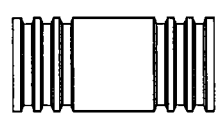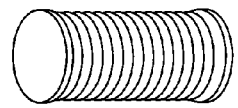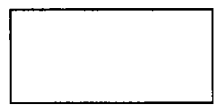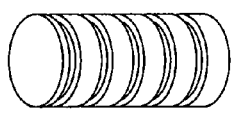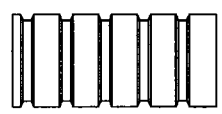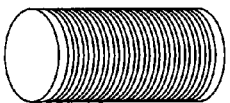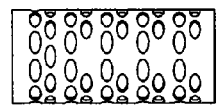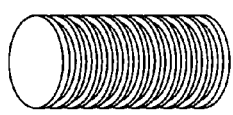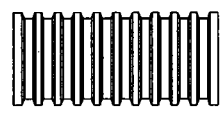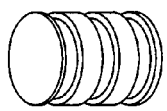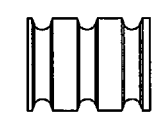

| Tensile Strength (N) | | | | |
|---|---|---|---|---|
| | ShapeLoc™ | Interference | Intrafix | Central Loc |
| μ | 831.9 | 631.6 | 644.3 | 691.1 |
| σ | 165.5 | 130.1 | 195.2 | 172.7 |

FIG. 20a

| Stiffness (N / mm) | | | | |
|---|---|---|---|---|
| | ShapeLoc™ | Interference | Intrafix | Central Loc |
| μ | 114.4 | 88.17 | 81.65 | 77.89 |
| σ | 13.9 | 6.79 | 16.5 | 7.07 |

FIG. 20b

| Slip Rate (μm / cycle) | | | | |
|---|---|---|---|---|
| | ShapeLoc™ | Interference | Intrafix | Central Loc |
| μ | 0.275 | 0.336 | 27.2 | 0.355 |
| σ | 0.043 | 0.074 | 31.6 | 0.046 |

FIG. 20c

SHAPE MEMORY POLYMER

CROSS REFERENCE TO RELATED APPLICATIONS

This application is a continuation of U.S. patent application Ser. No. 13/730,570 filed 28 Dec. 2012 entitled "Graft Fixation Device," which is a divisional of U.S. patent application Ser. No. 10/598,080 filed 7 Sep. 2006 entitled "Graft Fixation Device," which is a national stage filing of Patent Cooperation Treaty application no. PCT/US2006/012934 filed 3 Apr. 2006 entitled "A Graft Fixation Device and Method," which claims the benefit of priority pursuant to 35 U.S.C. §119(e) of U.S. provisional application No. 60/667,876 filed 1 Apr. 2005, each of which is hereby incorporated herein by reference in its entirety.

STATEMENT REGARDING FEDERALLY SPONSORED RESEARCH OR DEVELOPMENT

This invention was made with government support under Grant No. NIH-HL-067393 awarded by the National Institutes of Health. The government has certain rights in the invention.

BACKGROUND

Ligaments are strong fibrous soft tissue connecting the articular ends of bones to bind them together and to facilitate or limit motion. Injuries to ligaments are common, and patients who are physically active are generally more susceptible to such ligament injuries. The anterior cruciate ligament (ACL) of the knee joint is a ligament frequently injured by such patients. ACL injuries cause instability in the knee joint which, when left untreated, may lead to degenerative arthritis. Because of this condition, ACL reconstruction may be required. Generally during ACL reconstruction, a substitute soft tissue ligament or graft is attached to the femur (femoral fixation) and/or to the tibia (tibial fixation) to facilitate regrowth and permanent attachment.

There are several known methods for performing ACL reconstruction, and there are also several tibial or femoral fixation devices that may be used with these methods.

In surgery it is generally known to use soft tissue tendon grafts (e.g. hamstring tendon, taken from the thigh of the patient) to replace the severely damaged ACL. In a typical surgical procedure one end of a soft tissue graft is fixed into a drill hole made from the knee joint into the distal femur and another end of the graft is fixed into a drill hole made into the proximal tibia. The ends of the graft are fixed into the drill holes with fixation screws and in most cases with so-called interference screws. An interference screw may be a screw that has a larger diameter (including any grafts or tendons) than the cavity, thus generating a force that holds the tendon. A screw is installed into the space between the drill hole and the soft tissue grafts to lock the grafts into the drill hole. The tendon then acts as a new ACL.

There are several known methods for performing ACL reconstruction, and there are also several tibial or femoral fixation devices that may be used with these methods. The fixation screws, like interference screws, are normally made of metal like stainless steel or titanium, or of a bio-absorbable polymer like polylactide. An interference screw may be considered as metallic and/or bio-absorbable polymeric materials and composites, which are suitable for manufacturing of tendon graft fixation screws, are well known in the art, for example as described in the literature.

Conventional extra-articular hamstring graft fixation techniques have complications, such as suture stretch, graft tunnel motion and so-called windshield wiper effect where the size of the intra-articular drill hole end will increase due to graft movement in the drill-hole. Also the use of screws as fixation implants for soft tissue grafts in anterior crucial ligament procedures is complicated due to: 1) the threads of the screw cutting the grafts during screw installation if the screw is too big in relation to the tendon and/or if the space between the drill hole and tendon grafts is too small; 2) the threads of the screw damaging the tendon during screw installation; 3) the tendon rotating with the screw during screw installation so that the optimal position of the grafts is lost and/or the grafts are damaged; 4) divergence of the grafts and/or screw occurring; and 5) the bio-absorbable screw breaking during insertion.

SUMMARY

In one embodiment, the invention provides a fixation device, which may fix a soft tissue graft, like a tendon or ligament graft, to a bone with little risk of damaging the soft tissue graft during insertion.

One aspect is a device for use as a bone implant comprising, a body having a pre-implantation shape and a post-implantation shape different from the pre-implantation shape. The body is configured to change from the pre-implantation shape to the post-implantation shape in response to the body being activated. The body is configured to be inserted in a bone recess while the body is in the pre-implantation shape.

Another aspect is a method comprising inserting a cable member into a recess in a bone, inserting a retention device into the recess, the retention device containing a shape memory material, and activating the shape memory material.

Another aspect is a kit comprising a first bone implant. The first bone implant has a first pre-implantation shape and a first post-implantation shape different from the first pre-implantation shape. The first bone implant is configured to be inserted in a first bone recess while the first bone implant is in the first pre-implantation shape. The first bone implant is configured to fix a cable member to the first bone recess while the first bone implant is in the first post-implantation shape. The kit also comprises a second bone implant. The second bone implant has a second pre-implantation shape and a second post-implantation shape different from the second pre-implantation shape. The second bone implant is configured to be inserted in a second bone recess while the second bone implant is in the second pre-implantation shape. The second bone implant is configured to fix the cable member to the second bone recess while the second bone implant is in the second post-implantation shape. The second post-implantation shape is different from the first post-implantation shape.

Another aspect is a method comprising shaping a polymer material into a post-implantation shape and deforming the polymer material into a pre-implantation shape different from the post-implantation shape, while maintaining the temperature of the polymer material above a certain temperature. The method also comprises cooling the polymer material to below the certain temperature while holding the polymer material in the pre-implantation shape.

Another aspect is a kit comprising a first solution comprising a monomer, the first solution contained in a first container, a second solution comprising a cross-linker, the second solution contained in a second container. The kit also includes a cable member configured to function as a soft tissue replacement in a human body. The second solution is configured to form a third solution if the second solution is mixed with the first solution, wherein the third solution is capable of forming a shape memory polymer upon polymerization.

In another exemplary implementation, a polymerized composition is formed by a linear chain comprising an acrylate and a first cross-linker comprising a multi-functional acrylate. The polymerized composition exhibits a glass transition at a temperature between about 34° C. and about 50° C., inclusive. The polymerized composition exhibits shape memory effects.

In a further exemplary implementation, a device for in vivo medical applications is formed with a chemically-cross-linked, shape memory polymer. The shape memory polymer is composed of tert-butyl acrylate as a first monomer and polyethylene glycol dimethacrylate as a second chemically crosslinking monomer. The device is formed of the shape memory polymer in an original shape. The device is deformed from the original shape for use in the in vivo medical application. The device recovers to the original shape upon being placed in vivo at body temperature.

BRIEF DESCRIPTION OF THE DRAWINGS

FIGS. 7a-7h shows multiple forms of possible unconstrained shapes of devices.

FIG. 20a shows mean and standard deviations of tensile strengths of various fixation devices.

FIG. 20b shows mean and standard deviations of stiffnesses of various fixation options.

FIG. 20c shows mean and standard deviations of slip rates of various fixation options.

DETAILED DESCRIPTION

The following description of various embodiments is merely exemplary in nature and is in no way intended to limit the invention as claimed, its application, or uses.

An example of a joint repair surgery in which the following polymers, devices, methods and kits may be used is the repair of an ACL in a human knee. A ruptured ACL may be repaired through, in part, attaching a cable member the native posterior ACL attachment site (e.g., an opening of the tunnel at the site). For example, a cable member may be attached to the site via creating a bone recess and fixing the cable member to the bone recess. A bone recess may be used to increase the surface area of bone to which the cable member may be fixed.

A technique in the prior art for fixation of an ACL soft tissue graft includes drilling a properly sized tunnel from the anteromedial tibial metaphysis into the native posterior ACL attachment site, feeding a soft tissue graft into the tunnel, and fixing the soft tissue graft to the tunnel via an interference screw driven into the tunnel against the soft tissue graft.

Another technique in the prior art includes drilling a tunnel in a tibia and placing an anchor with an attached suture into the tunnel thus anchoring the suture in the bone. The suture is then attached to the soft tissue graft.

Figure 1:
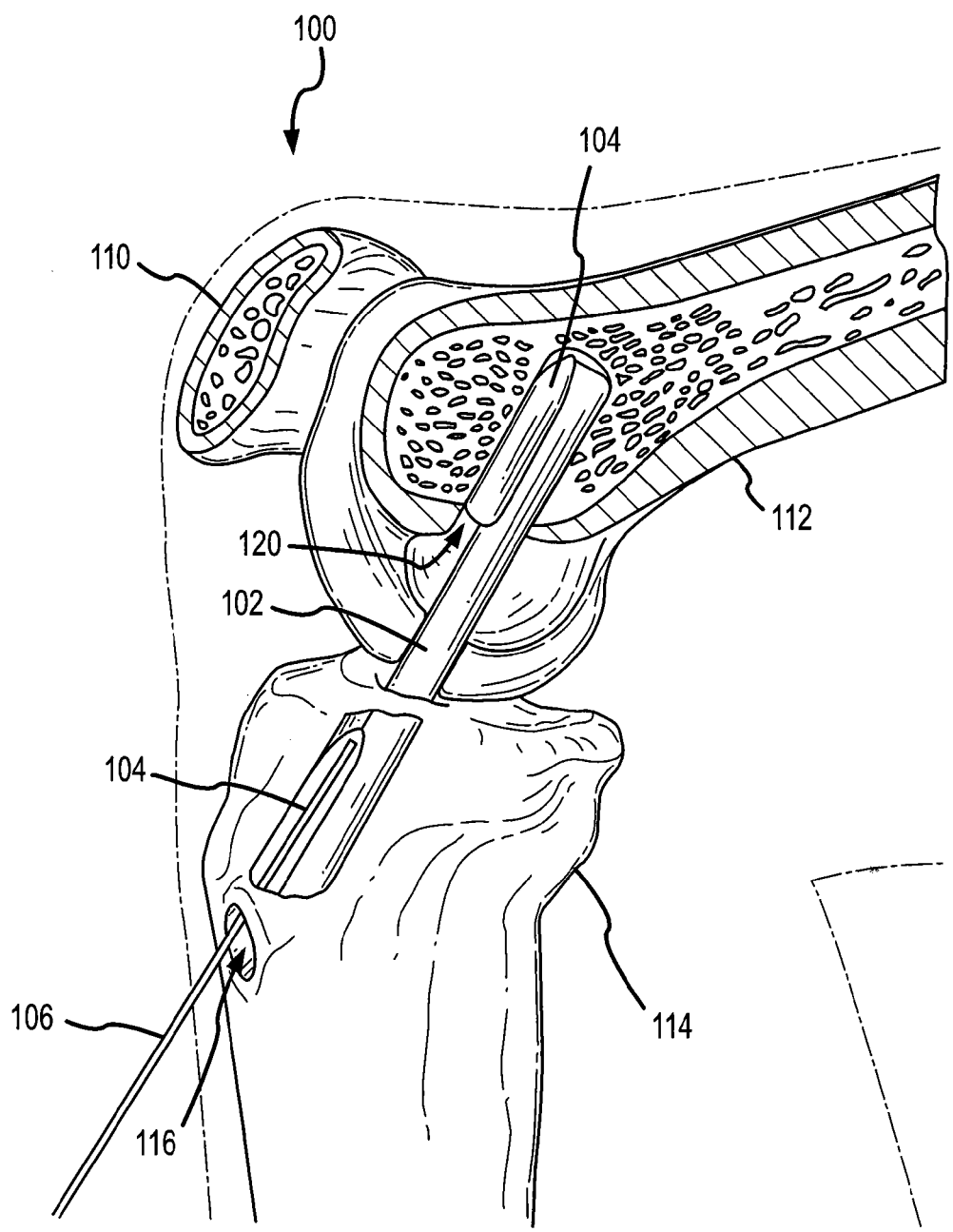
FIG. 1 shows a cross-section of an embodiment of an anterior cruciate ligament repair site.

FIG. 1 shows a cross-section of an embodiment of an anterior cruciate ligament (ACL) repair site 100. The ACL repair site 100 comprises a patella 110, a femur 112, and a tibia 114. A tibia recess 116 has been created in the tibia 114, and a femur recess 120 has been created in the femur 112. A cable member 102 is partially inside both the tibia recess 116 and the femur recess 120. Devices 104 are inside each of the tibia recess 116 and the femur recess 120.

A surgeon or other practitioner may insert devices 104 into either or both of the tibia recess 116 and the femur recess 120 using an insertion device 106. In one embodiment, the insertion device 106 is a guide wire that may aid in the insertion of a device 104. For example, a device 104 may be threaded onto a guide wire (e.g., the guide wire enters the device through one opening in the device and exits through another opening in the device), and the device may be pushed into an installed position along the guide wire. In another embodiment, the insertion device 106 is a shaft that may be used to push the device 104 into place. For example, a cavity in the device 104 may accept the insertion device 106, allowing the insertion device (e.g., shaft) to couple with the device, guide the device and move the device into an installed position. As another example, the device 104 may be attached to the insertion device 106 and the device 104 and insertion device 106 may be separated (e.g., when the device is in an installed position).

In the embodiment shown in FIG. 1, the devices 104 are substantially smooth and have narrow tips in the pre-implantation shape (shown). In another embodiment, the devices 104 have a shorter, wider shape in the post-implantation shape (not shown).

The devices 104 shown in FIG. 1 represent one embodiment of a device which may be used to repair an ACL in this manner. Numerous other embodiments of devices and modifications to devices similar to the devices 104 shown in FIG. 1 are described herein. For example, any of the embodiments described herein of devices, methods and polymers may be used to repair an ACL.

The descriptions of devices, methods and polymers herein should not be understood to be limited only to the Figures or to any specific Figure. Therefore, the devices shown in FIG. 1 may be used as shown in other Figures or may otherwise be used, and the devices shown in other Figures or otherwise described may be used in FIG. 1 or may otherwise be used.

In the embodiment shown, the cable member 102 is used to replace a torn or failed ACL. The cable member is held by the devices 104 at points (e.g., artificial attachment sites) in the tibia 114 and the femur 112. The cable member 102 may comprise any suitable material, as described further herein.

An ACL repair in a knee is discussed here as an example of a surgery site where a device and/or method of the present invention may be employed. Other sites, joints and parts of anatomy may have surgery performed on them using a polymer, device or method of the present invention. For example, the devices and methods described herein can be used for rotator cuff reconstruction, for acromioclavicular (AC) reconstruction, for ACL reconstruction and for fastening tendons, grafts, or sutures to other tissue, such as bone or other soft tissue.

Common weaknesses with the ACL replacement methods practiced in sports medicine industry are caused by the fixation device and how it is used. For example, the fixation device may be the source of failure for the surgery by allowing a cable member (e.g., tendon) to slip. The fixation device may also cause a cable member to break. For example, an interference screw may cut into or entirely through the cable member during the process of insertion into the bone tunnel.

A cable member as used herein may be a tendon, ligament, artificial soft tissue replacement, a metal wire, a composite structure, synthetic fiber or any member that may be used to create a substitute for an animal soft tissue (e.g., tendon, ligament, fascia, vessel).

Figure 2:
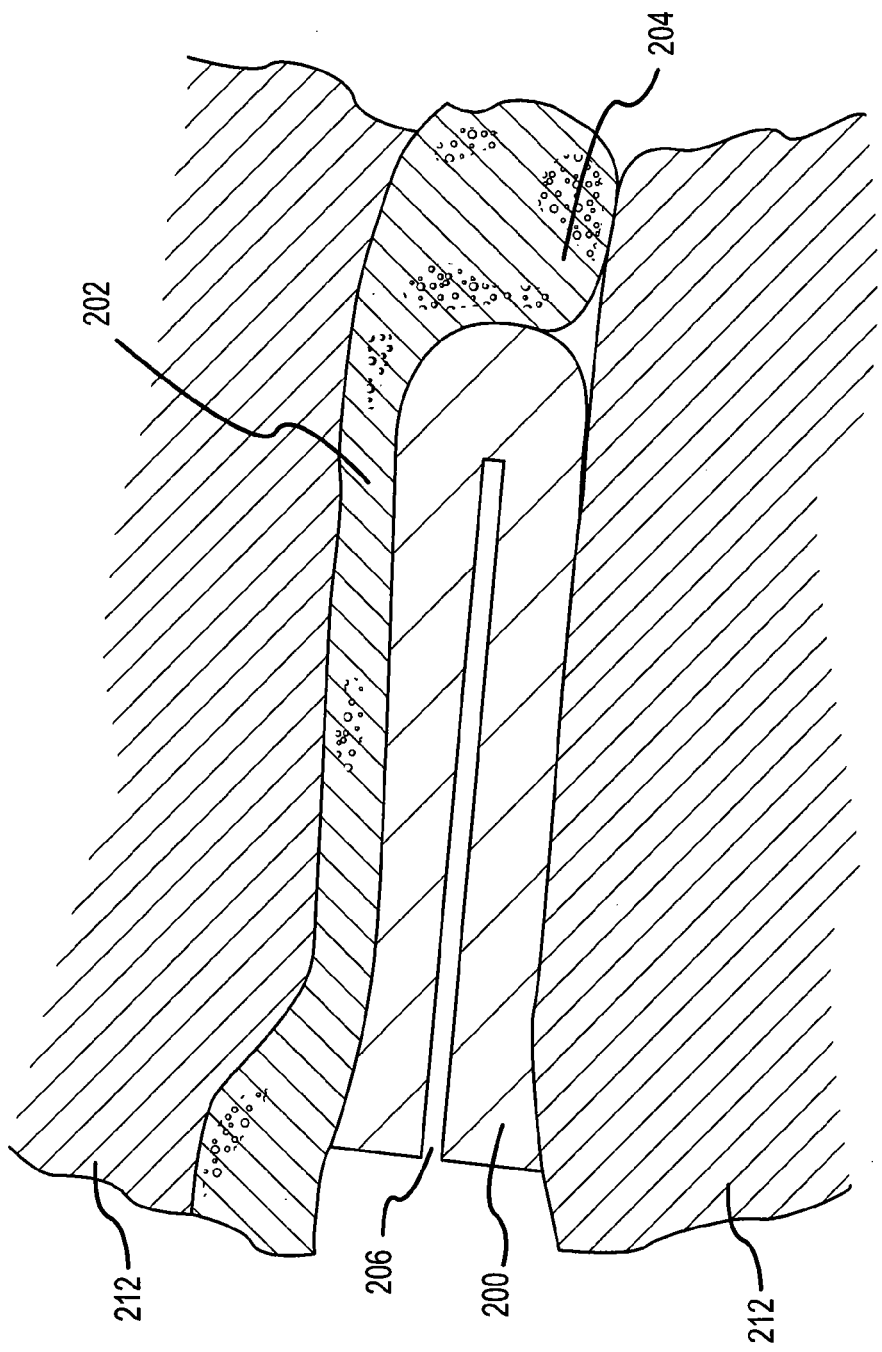
FIG. 2 shows a cross-section of a device installed and in a post-implantation shape with a cable member in a bone recess.

FIG. 2 shows a cross-section of a device 200 installed and in a post-implantation shape with a cable member 202 in a bone recess 204. The device 200 comprises a cavity 206. The device 200 presses the cable member 202 against a wall of the bone recess 204 thereby using friction (e.g., friction between the wall and the cable member, friction between the device and the cable member, friction between the device and the wall) to fix the cable member to a bone 212.

The device 200 may be inserted into the bone recess 204 in a pre-implantation shape that is different from the post-implantation shape. In one embodiment, the device 200 comprises a shape memory material. The shape memory material allows the device 200 to change from the pre-implantation shape to the post-implantation shape. For example, after the device is placed within a bone recess, the shape memory material may be activated into a post-implantation shape. In another embodiment, the device 200 comprises an elastomer. The elastomer allows the device 200 to change from the pre-implantation shape to the post-implantation shape. For example, the device 200 may be placed within a bone recess 204 while the is elastomer constrained by a constraining member. The removal (e.g., separating, dissolving) of the constraining member may allow the elastomer to change into a post-implantation shape. In yet another embodiment, another material may be used to allow the device 200 to change from a pre-implantation shape to a post-implantation shape.

The discussion herein of shape memory materials and devices that use shape memory materials may be understood as an example of how a device may be used with a pre-implantation shape and a post-implantation shape to fix a cable member as part of a surgical procedure. The use of shape memory materials is not meant to exclude the analogous use of elastomer materials or other appropriate materials.

The post-implantation shape may be a function of the bone recess 204 and the cable member 202 as installed with the device. A device may also have an unconstrained shape that the device would embody if it were activated with little or no constraints on the device's shape (e.g., the device resting on a table, the device in a water bath, the device resting on a heating plate). The post-implantation shape may be a function of the device's unconstrained shape. For example, the device may exert a force (e.g. stress) on a cable member and/or a bone recess based on the difference between the post-implantation shape of the device and the unconstrained shape of the device (e.g., the difference may represent the strain on the device caused by the deformation still present in the device, as installed, after activation).

A device may have different post-implantation shapes based on particular installation. To the extent that the stress (e.g. forces transmitted from the bone recess 204 and the cable member 202) induce strain on the device, the device's post-implantation shape may be determined by the particular installation and installation procedure of the cable member and determined by the particular bone recess. In one embodiment, the pre-implantation shape is substantially different from the device's post-implantation shape. In another embodiment, some elements of the device do not change significantly between the device's pre-implantation shape and the post-implantation shape.

As used herein the term "bone recess" may comprise any volume at least partially defined by a bone wall. For example, a bone recess may be a hole in a bone, a pre-existing configuration of a bone, a configuration between two bones, or a configuration between two boney structures. In one embodiment, a bone recess 204 is a tunnel drilled into a bone 212. In another embodiment, a bone recess comprises a space between two bones in a joint (not shown). For example, a bone recess within a joint may accept a device in a pre-implantation shape and the bone recess within the joint may be spread by the activation of the device into a post-implantation shape. In yet another embodiment, a bone recess is an irregular cavity in a bone (not shown). For example, a bone recess may be a fracture in a bone or a milled shelf in a bone.

Shape memory materials may recover a predetermined shape after mechanical deformation, exhibiting a shape memory effect. A shape memory effect is often initiated by a change in temperature and has been observed in metals, ceramics, and polymers. However, a shape memory effect may be initiated by another cause. From a macroscopic point of view, the shape memory effect in polymers may differ from ceramics and metals due to the lower stresses and larger recoverable strains sometimes achieved in polymers.

For example, a polymer is a shape memory polymer (SMP) if the original shape (e.g., an unconstrained shape) of the polymer body may be recovered by heating the body without substantial constraints above a shape recovery temperature, a glass transition temperature, or deformation temperature ($T_d$), even if the original shape of the polymer has been destroyed mechanically at a lower temperature than $T_d$, or if the memorized shape (e.g., the unconstrained shape) is recoverable by application of another stimulus. Any polymer that can recover an original shape from a temporary shape (e.g., a pre-implantation shape) by application of a stimulus such as temperature may be considered a SMP. The original shape is set by manufacture and the temporary shape is set by thermo-mechanical deformation.

A SMP may have the ability to recover large deformation upon heating. In one embodiment, a device with a memorized shape (e.g., original shape) is made from a SMP, which can subsequently be crushed or deformed and inserted into a bone recess, used to hold a graft, and the device is deployed (e.g., expanded, contracted) by increasing the temperature of the device. In one embodiment, the device's deployment may be controlled by controlling the temperature of the device.

However, the shape memory effect of a shape memory material is different from, and usually greater in terms of absolute effect, than the thermal expansion of a material. Those with skill in the art will understand the differences and similarities between shape memory effects and thermal expansion effects.

The thermomechanical response of shape memory polymers may be defined by four critical temperatures. The glass transition temperature, $T_g$, is typically represented by a transition in modulus-temperature space and can be used as a reference point to normalize temperature. Shape memory polymers offer the ability to vary $T_g$ over a temperature range of several hundred degrees by control of chemistry or structure. The pre-deformation temperature, $T_d$, is the temperature at which the polymer is deformed into its temporary shape. Depending on the required stress level and strain level, the initial deformation at $T_d$ can occur above or below $T_g$. The storage temperature, $T_s$, represents the temperature in which no shape recovery occurs. $T_s$ is often equal to or below $T_d$. At the recovery temperature, $T_r$, the shape memory effect is activated, which causes the material to recover its original shape, and is typically in the vicinity of $T_g$ or above. Therefore, $T_s$ is often below $T_g$ because shape recovery begins at $T_r$. In an embodiment, recovery may be accomplished isothermally by heating to a fixed $T_r$ and then holding, or by continued heating up to and past $T_r$.

Generally, a transition temperature may be a characteristic of a material (e.g., SMP, thermoplastic, thermoset) and may be defined in a number of ways. For example, a transition temperature may be defined by a temperature of a material at the onset of a transition, the midpoint of a transition, or the completion of a transition. As another example, a transition temperature may be defined by a temperature of a material at which an inflection point of the modulus of a material (e.g., peak tan-delta).

A transition temperature may be represented by a glass transition temperature, a melting point, or another temperature related to a change in a process in a material or a characteristic of a material.

A transition temperature may be related to a number of processes or characteristics. For example, a transition temperature may relate to a transition from a stiff (e.g., glassy) behavior to a rubbery behavior of a material. As another example, a transition temperature may relate to a melting of soft segments of a material.

The processes and characteristics relating to a transition temperature may be microscopic or macroscopic. For example, a transition temperature may relate to molecule mobility or microscopic material structure. As another example, a transition temperature may relate to the strength of molecular bonds As yet another example, a transition temperature may relate to a modulus of the material.

In addition, the microscopic processes, including those processes around a transition temperature, may be related to the macroscopic properties of the material. Indeed, one method of determining whether a microscopic process is occurring (or has occurred) is to monitor macroscopic processes or characteristics. Microscopic characteristics are commonly related to macroscopic characteristics, and macroscopic characteristics are commonly monitored as a substitute for monitoring microscopic characteristics.

From a macroscopic viewpoint, a polymer often has a shape memory effect if it possesses a glass transition, a modulus-temperature plateau in the rubbery state, and a difference between the maximum achievable strain, $\epsilon_{max}$, during deformation and permanent plastic strain after recovery, $\epsilon_p$. The difference $\epsilon_{max}-\epsilon_p$ is defined as the recoverable strain, $\epsilon_{recover}$, while the recovery ratio is defined as $\epsilon_{recover}/\epsilon_{max}$.

The microscopic mechanism responsible for shape memory in polymers depends on both chemistry and structure. A cause of shape recovery in polymers is the low conformational entropy state created and subsequently frozen during the thermomechanical cycle. If the polymer is deformed into its temporary shape at a temperature below $T_g$, or at a temperature where some of the hard polymer regions are below $T_g$, then internal energy restoring forces will also contribute to shape recovery. In either case, to achieve shape memory properties, the polymer often has some degree of chemical crosslinking to form a "memorable" network or may contain a finite fraction of hard regions serving as physical crosslinks.

Polymers may be selected based on the desired glass transition temperature(s) (e.g., at least one segment is amorphous) or the melting point(s) (e.g., at least one segment is crystalline), which in turn is based on the desired applications, taking into consideration the environment of use. Shape memory polymers may be designed for use in medical devices. Design decisions may depend on the targeted body system and other device design constraints such as required in-vivo mechanical properties.

For example, a SMP may be designed so that the polymer transition temperature is near a standard human body temperature (e.g., $T_r \sim T_g \sim 37°$ C.) thereby using a body's thermal energy to activate the SMP. The mechanical properties (e.g. stiffness) of the SMP material often depend on $T_g$. Those with skill in the art will recognize that designing a stiff SMP device when the polymer $T_g$ is close to a standard human body temperature may be difficult due to the compliant nature of the polymer.

In an embodiment, the required storage temperature, $T_s$, of a shape memory polymer with $T_g \sim 37°$ C. will possibly be below room temperature requiring "cold" storage prior to deployment. A shape memory polymer may also be designed so that the recovery temperature is higher than a standard human body temperature $T_r \sim T_g > 37°$ C. In one embodiment, the glass transition temperature of the SMP is about 48° C. Those with skill in the art will recognize that the storage temperature may be equal to room temperature thereby facilitating storage of the device and reducing unwanted deployments. A higher recovery temperature than ~37° C. may require localized heating of the SMP to induce recovery of the SMP. Damage to some cells in the human body may occur at temperatures about 5 degrees Celsius above the body temperature through a variety of mechanisms including apoptosis and protein denaturing. Local heating "bursts" may be used to minimize exposure of human cells to elevated temperatures and to circumvent cell damage through over-heating.

SMPs may have biocompatibility with different areas of the body. For example, FDA approved dental materials may not be biocompatible in a cardiovascular environment. Polyethyleneglycol (PEG), a form of which is also known as polyethylene oxide (PEO), has been studied for its protein and cell resistance, which renders a non-fouling surface. Polylactic acid (PLA) as well as polyglycolic acid (PLGA) have already been FDA approved in devices such as interference screws and suture materials. However, there may be some concerns about PLA being hydrolytically broken down into lactic acid, which could potentially cause an inflammatory response in surrounding cells. Nonetheless, PEG copolymerized with PLA (PEG-co-PLA) may form a cross-linked hydrogel. These hydrogels may be modified with methacrylate groups to achieve a wide range of properties. PEG modified with methacrylates have shown biocompatibility with tissue engineering. Other biodegradable polymers are polypropylene-fumarate-co-ethyleneglycol, polycaprolactone, polyanhydrides, and polyphosphazenes.

SMP polymer segments may be natural or synthetic. The polymer segments may be biodegradable or non-biodegradable. Biodegradable materials may degrade by hydrolysis, by exposure to water or enzymes under physiological conditions, by surface erosion, by bulk erosion, or a combination thereof. Non-biodegradable polymers used for medical applications may not include aromatic groups other than those present in naturally occurring amino acids.

The polymer may be in the form of a hydrogel (typically absorbing up to about 90% by weight of water). The polymer may also be ionically crosslinked with multivalent ions or polymers. Ionic crosslinking between soft segments can be used to hold a structure, which, when deformed, can be reformed by breaking the ionic crosslinks between the soft segments. The polymer may also be in the form of a gel in solvents other than water or aqueous solutions. In these polymers, a temporary shape can be fixed by hydrophilic interactions between soft segments.

Representative natural polymer blocks or polymers include proteins such as zein, modified zein, casein, gelatin, gluten, serum albumin, and collagen, and polysaccharides such as alginate, celluloses, dextrans, pullulane, and polyhyaluronic acid, as well as chitin, poly(3-hydroxyalkanoate)s, especially poly(.beta.-hydroxybutyrate), poly(3-hydroxyoctanoate) and poly(3-hydroxyfatty acids). Representative natural biodegradable polymer blocks or polymers include polysaccharides such as alginate, dextran, cellulose, collagen, and chemical derivatives thereof (substitutions, additions of chemical groups, for example, alkyl, alkylene, hydroxylations, oxidations, and other modifications routinely made by those skilled in the art), and proteins such as albumin, zein and copolymers and blends thereof, alone or in combination with synthetic polymers.

Representative synthetic polymer blocks or polymers include polyphosphazenes, poly(vinyl alcohols), polyamides, polyester amides, poly(amino acid)s, synthetic poly (amino acids), polyanhydrides, polycarbonates, polyacrylates, polyalkylenes, polyacrylamides, polyalkylene glycols, polyalkylene oxides, polyalkylene terephthalates, polyortho esters, polyvinyl ethers, polyvinyl esters, polyvinyl halides, polyvinylpyrrolidone, polyesters, polylactides, polyglycolides, polysiloxanes, polyurethanes and copolymers thereof. Examples of suitable polyacrylates include poly (methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate) and poly(octadecyl acrylate).

Synthetically modified natural polymers include cellulose derivatives such as alkyl celluloses, hydroxyalkyl celluloses, cellulose ethers, cellulose esters, nitrocelluloses, and chitosan. Examples of cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt. These are collectively referred to herein as "celluloses".

Representative synthetic degradable polymer segments include polyhydroxy acids, such as polylactides, polyglycolides and copolymers thereof; poly(ethylene terephthalate); polyanhydrides, poly(hydroxybutyric acid); poly(hydroxyvaleric acid); poly[lactide-co-(.epsilon.-caprolactone)]; poly[glycolide-co-(.epsilon.-caprolactone)]; polycarbonates, poly(pseudo amino acids); poly(amino acids); poly(hydroxyalkanoate)s; polyanhydrides; polyortho esters; and blends and copolymers thereof. Polymers containing labile bonds, such as polyanhydrides and polyesters, are well known for their hydrolytic reactivity. Hydrolytic degradation rates of these polymers may be altered by simple changes in the polymer backbone and the polymer's sequence structure.

Examples of non-biodegradable synthetic polymer segments include ethylene vinyl acetate, poly(meth)acrylic acid, polyamides, polyethylene, polypropylene, polystyrene, polyvinyl chloride, polyvinylphenol, and copolymers and mixtures thereof.

Hydrogels can be formed from polyethylene glycol, polyethylene oxide, polyvinyl alcohol, polyvinyl pyrrolidone, polyacrylates, poly(ethylene terephthalate), poly(vinyl acetate), and copolymers and blends thereof. Several polymeric blocks, for example, acrylic acid, are elastomeric only when the polymer is hydrated and hydrogels are formed. Other polymeric blocks, for example, methacrylic acid, are crystalline and capable of melting even when the polymers are not hydrated.

Either type of polymeric block can be used, depending on the desired application and conditions of use. For example, shape memory is observed for acrylic acid copolymers largely in the hydrogel state, because the acrylic acid units are substantially hydrated and behave like a soft elastomer with a very low glass transition temperature. The dry polymers do not exhibit significant shape memory effects. When dry, the acrylic acid units behave as a hard plastic even above the glass transition temperature and show little change in mechanical properties on heating. In another example, copolymers including methyl acrylate polymeric blocks as the soft segments show shape memory properties even when dry.

The polymers can be obtained from commercial sources such as Sigma Chemical Co., St. Louis, Mo.; Polysciences, Warrenton, Pa.; Aldrich Chemical Co., Milwaukee, Wis.; Fluka, Ronkonkoma, N.Y.; and BioRad, Richmond, Calif. Alternately, the polymers can be synthesized from monomers obtained from commercial sources.

In an embodiment, SMPs may be photopolymerized from tert-butyl acrylate (tBA) di-functional monomer with polyethylene glycol dimethacrylate (PEGDMA) tetra-functional monomer acting as a crosslinker. A di-functional monomer may be any compound having a discrete chemical formula further comprising an acrylate functional group that will form linear chains. A tetra-functional monomer may be any compound comprising two acrylate, or two methacrylate groups. A crosslinker may be any compound comprising two or more functional groups (e.g., acrylate, methacrylate). Also, ethyleneglycol, diethyleneglycol, and triethyleneglycol based acrylates are forms of polyethyleneglycol based acrylates with one, two, or three repeat units.

A functional group may refer to any reactive group. For example, a functional group may be an acrylate group. A mono-functional molecule refers to a molecule having one functional group (e.g., an acrylate group, a methacrylate group). A multi-functional molecule may have two or more functional groups.

In one embodiment, the SMP material is a photo-initiated network comprising of tert-butyl acrylate (tBA), polyethyleneglycol dimethacrylate (PEGDMA), and 2,2-dimethoxy-2-phenylacetephenone as a photo-initiator. The glass transition temperature ($T_g$) may be tailored to a $T_g$~48° C. through controlling the amount of cross-linking PEGDMA. A $T_g$ of roughly 48° C. is a useful $T_g$ for shape recovery within a human body temperature.

Those with skill in the art will recognize that other polymerization techniques, such as thermal radical initiation, can be used for polymer fabrication.

Figure 24:
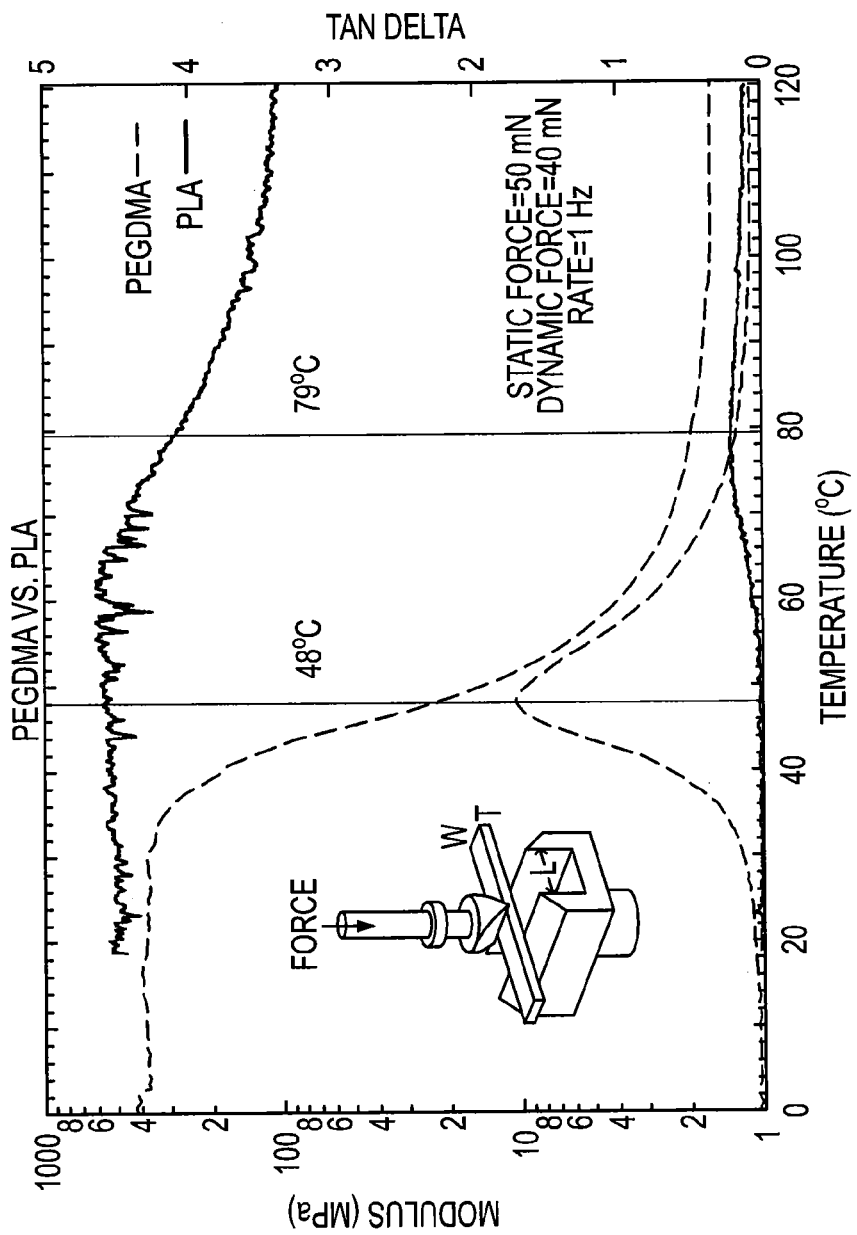
FIG. 24 shows a schematic of the three-point flexure thermomechanical setup and the results of a Dynamic Mechanical Analysis (DMA) test showing storage modulus and tan-delta as a function of temperature for the PEGDMA copolymer and PLA.

Shape memory properties of a class of polymers with a high degree of biocompatibility may be investigated using a three-point flexure testing apparatus (as shown in FIG. 24) to investigate the thermomechanics of the shape memory effect under various conditions. The experimental results below form a foundation for understanding the effects of pre-deformation temperature, constraint level, and recovery temperature/time on the shape memory effect in a biocompatible polymer system. The examples and embodiments described herein are meant to illustrate, not to limit, the present invention.

Other potential applications of biocompatible shape memory polymers, which capitalize on some of the observed thermomechanical behaviors include rotator cuff reconstruction, for acromioclavicular (AC) reconstruction, for anterior cruciate ligament reconstruction (ACL) and generally for fastening tendons, grafts, or sutures to tissue, including soft tissue and bone.

In an alternate embodiment (not shown) the device has a substantially cylindrical cross-section with ridges. The ridges are just an example of shapes and shape features that may be used to aid in fixing the device to the bone recess and/or the cable member. For example, baffles, flaps, screw-like threads and/or bumps may be used to aid the fixation of the device to the bone recess and/or the cable member. The below description of ridges, therefore, should be understood to apply to all types of shapes and shape features of a device.

Ridges may be part of the device's shape in order to increase the device's contact surface area, for example, between the device (e.g., 200) and the cable member (e.g., 202) or between the device and the bone recess. In one embodiment, ridges may be configured to conform to the bone recess, providing a more solid fixation force between the bone recess and the device.

In one embodiment, the ridges may be part of the device's pre-implantation shape. In another embodiment, the ridges may be part of the device's post-implantation shape. In yet another embodiment, the ridges may be part of both the device's pre-implantation shape and the device's post-implantation shape.

In one embodiment, the cable member may conform to the ridges, providing increased contact surface area between the device and the cable member. In another embodiment, the device may conform to the cable member or the bone recess. In yet another embodiment, the device and the cable member (and/or the bone recess) may conform, to some extent, to each other.

The device 200 may also have surface features (not shown), such as textures or porosity. For example, surface features may be provided for physical purposes, such as increasing the fixing forces provided by the device. In one embodiment, the surface features are on the shape memory material. In another embodiment, the surface features are on a part of the device that is not a shape memory material. In one embodiment, the surface features may increase friction between a cable member and the device. In another embodiment, the surface features may increase friction between a part of the bone recess and the device.

Surface features may also be provided for physiological purposes. For example, surface features may be provided to encourage bone in-growth. In one embodiment, surface features are configured in a manner that encourages bone deposits and the surface features may hold bone-growth stimulants. In another embodiment, surface features are configured in a manner that encourages bio-compatability. In yet another embodiment, surface features are configured in a manner that encourages soft tissue growth.

The device 200 may have a curved or otherwise shaped tip to ease insertion into the bone recess with a cable member. In one embodiment, the device has a curved tip in the device's pre-implantation shape. In another embodiment, the device has a curved tip in the device's pre-implantation shape and a differently curved tip in the device's post-implantation shape.

In one embodiment, the device 200 has a cavity 206. In one embodiment, the cavity 206 is configured to accept a heating element (not shown) to aid in the application of heat to a shape memory material contained in the device. For example, the cavity 206 may be spaced from the outer surfaces of the device 200 that contact cells that surround the device (e.g., living cells, human cells) that may be damaged by heating. Spacing of the cavity from outer surfaces of the device may allow activation of a shape memory material in manners that limit the amount of heat transferred to surrounding cells. Inner walls of the cavity 206 may be contacted using a heating element (not shown) to supply heat to the inner walls of the cavity. Certain methods may be used to reduce the heat transferred to surrounding cells. For example, a method of using heating "bursts" may be employed to limit heat transfer to surrounding cells.

In another embodiment, the cavity 206 is configured to accept a drug, a bone cement, suture material, or another material. For example, a material may be inserted into the device 200 after the device has been inserted into the bone recess 204. Delivery of material inserted into the device may be achieved through absorption by the device, or through channels as described further below. In yet another embodiment, the cavity 206 is configured to accept a heating element and is configured to accept material after the shape memory material has been activated. For example, a shape memory material may not have significant channels before being activated (e.g., in the material's pre-implantation shape), and the shape memory material may have channels after being activated (e.g., in the material's post-implantation shape).

In another embodiment, the cavity 206 is configured to hold a guide wire to aid insertion of the device 200. For example, the guide wire may be used as is shown in FIG. 1. In one embodiment, the cavity 206 has one opening on each of two ends of the device 200 while the device is in its pre-implantation shape, allowing a guide wire to be threaded through the device. In another embodiment, the cavity 206 has one opening on each of two ends of the device 200 while the device is in its pre-implantation shape, and the cavity 206 has only one opening on one end of the device while the device is in its post-implantation shape. In yet another embodiment, the cavity 206 has another opening that does not change shape during the device's change from the device's pre-implantation shape to the device's post-implantation shape.

The device 200 may come in a kit that also includes a packaging (not shown) that is removed before being inserted. The packaging may maintain a sterile environment around the device 200. For example, the packaging may surround the device. In one embodiment, the packaging is a form-fitting packaging such as a shrink-wrap packaging. For example, the packaging may provide a force resisting deployment of the device from its pre-implantation shape to its post-implantation shape (e.g., through shape memory effect, through an elastomeric response) before an appropriate time (e.g., installation). In another embodiment, the packaging encloses the device 200 with another material. For example, the packaging may enclose the device in a sterile fluid or gas (e.g. a pressurized compressible gas).

Figure 3:
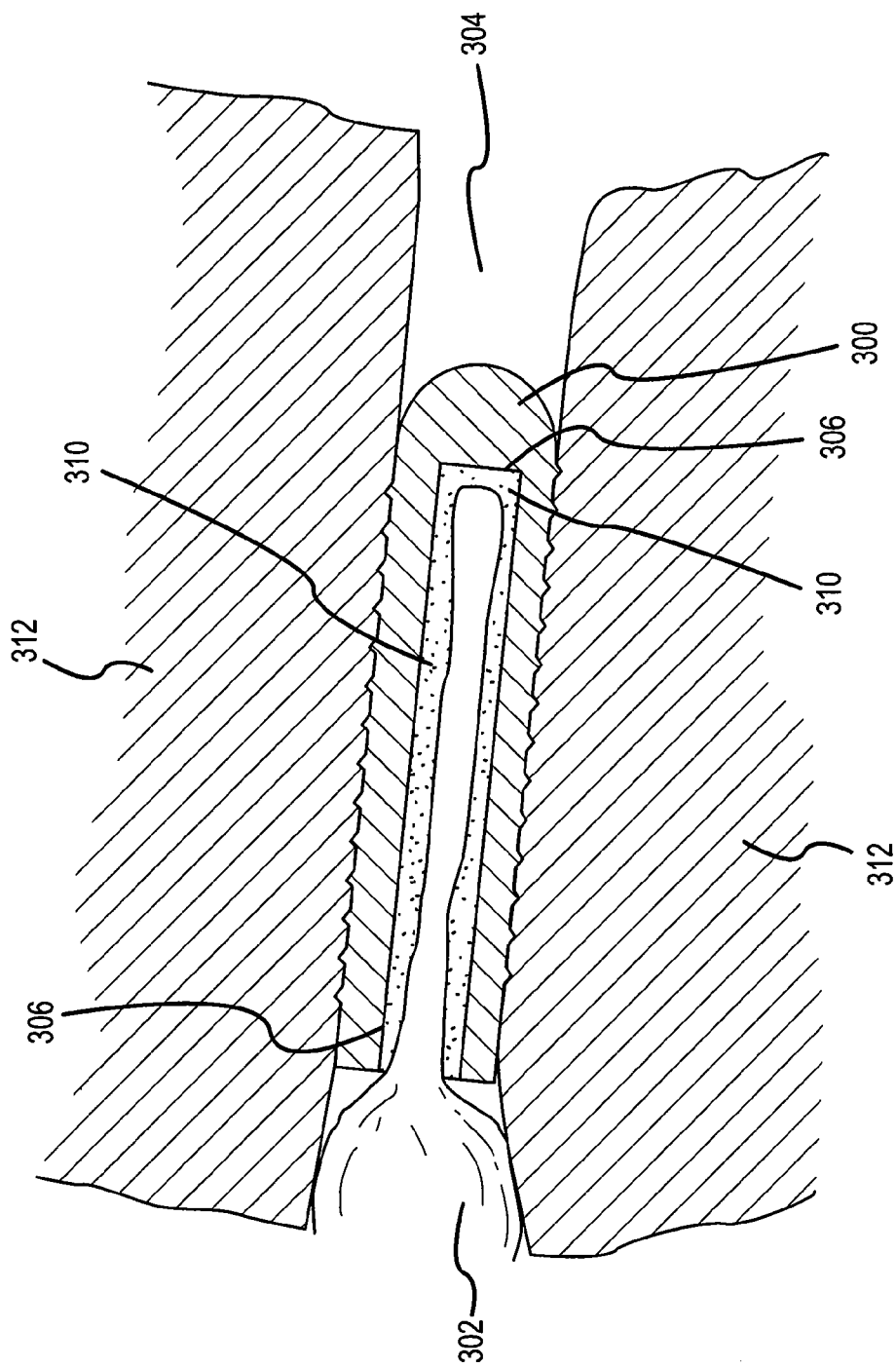
FIG. 3 shows a cross-section of another embodiment of a device installed and in a post-implantation shape with a cable member in a bone recess.

FIG. 3 shows a cross-section of another embodiment of a device 300 installed and in a post-implantation shape with a cable member 302 in a bone recess 304 in a bone 314. The device 300 fixes the cable member 302 to the device 300 inside a cavity 306 within the device. The cavity 306 within the device 300 is at least partially defined by a fixation element 310.

The device 300 may incorporate any of the properties or elements of other devices described herein.

The device 300 is configured to interface with a bone recess 304 and fix the cable member 302 to the bone thereby. In one embodiment, the device 300 is configured to fix a cable member to the device before interfacing (e.g., through insertion) with the bone recess. In another embodiment, the device is configured to interface with a bone recess and be fixed to the bone recess before accepting and fixing a cable member in the cavity 306. In yet another embodiment, the device is configured so that either the cable member may be fixed to the device first or the device may be fixed to the bone recess first.

The fixation element 310 may be constructed in many manners. In one embodiment, the fixation element comprises by a solid body. In another embodiment, the fixation element comprises a liquid that is transformed (e.g., polymerized, cured) into a solid body to hold a cable member after the cable member is inserted. In this case, the device 300 may also be the mold in which the liquid is transformed.

Such a transformable liquid may be provided in a kit with the device 300 in separate containers that must be mixed to create the transformable liquid. The kit allows a surgeon to create the device at the time of surgery in order to form the device into the shape necessary to fix the cable member in the bone recess 304.

For example, one or more monomers and cross-linkers may be provided in separate containers in a kit that when mixed may be polymerized or may automatically polymerize. In an embodiment, the polymer created may be a shape memory polymer. Such a kit may also include a cable member configured to function as a soft tissue replacement in a human body and the cable member may be further configured to be partially encapsulated in the shape memory polymer. As discussed in greater detail herein, the cable may be made from one or more of an animal tissue, a synthetic fiber, a natural fiber, a polymer, a metallic wire, a bundle, or a composite.

Such a kit may also include a polymerizing device to initiate the polymerization reaction, such as for example, a radiation source, an ultraviolet light source, a heating source, and a source of electrical current. Alternatively, the polymerization may be automatic or caused by a heat generated by the ambient environment or the patient. Other devices may also be included in the kit to assist the surgeon, such as a mixing element like a spatula, one or more metering devices for metering precise amounts of monomer and crosslinking solutions, mixing vessels or plates which may also server dual purposes such as a mold or a heat conductor or insulator, and a support configured to hold the cable member.

In yet another embodiment, the fixation element comprises a body (e.g., a spring member) that folds or collapses upon itself in response to a force (not shown) to hold the cable member, thereby allowing the cable member to be inserted but not removed.

The fixation element 310 may adapt to accommodate a cable member 302 when it is inserted. For example, the fixation element 310 may be deformed (e.g., strained) by the cable member 302 as the cable member is inserted into the cavity within the device and the stress between the cable member and the fixation element may help fix the cable member to the device. The cable member may also be deformed (e.g., strained) by the fixation element 310 as the cable member is inserted into the cavity within the device and the resulting stress between the cable member and the fixation element may help fix the cable member to the device.

The fixation element 310 may comprise a shape memory material (e.g., a SMP). A shape memory material may be used in the fixation element to provide a source of strain and/or stress after insertion of the cable member. For example, a cable member may be inserted into the cavity and a stress/strain relationship between the cable member and the fixation element may be established as described herein. The shape memory material contained in the fixation device may then be activated to produce a different stress/strain relationship between the cable member and the fixation device. The activation of shape memory materials and the stresses and strains produced as a result of activation are discussed further herein.

Shape memory materials may be used in other parts of the device as well. For example, shape memory materials may be used to aid in fixing the device to the bone recess as described in greater detail herein.

Figure 4:
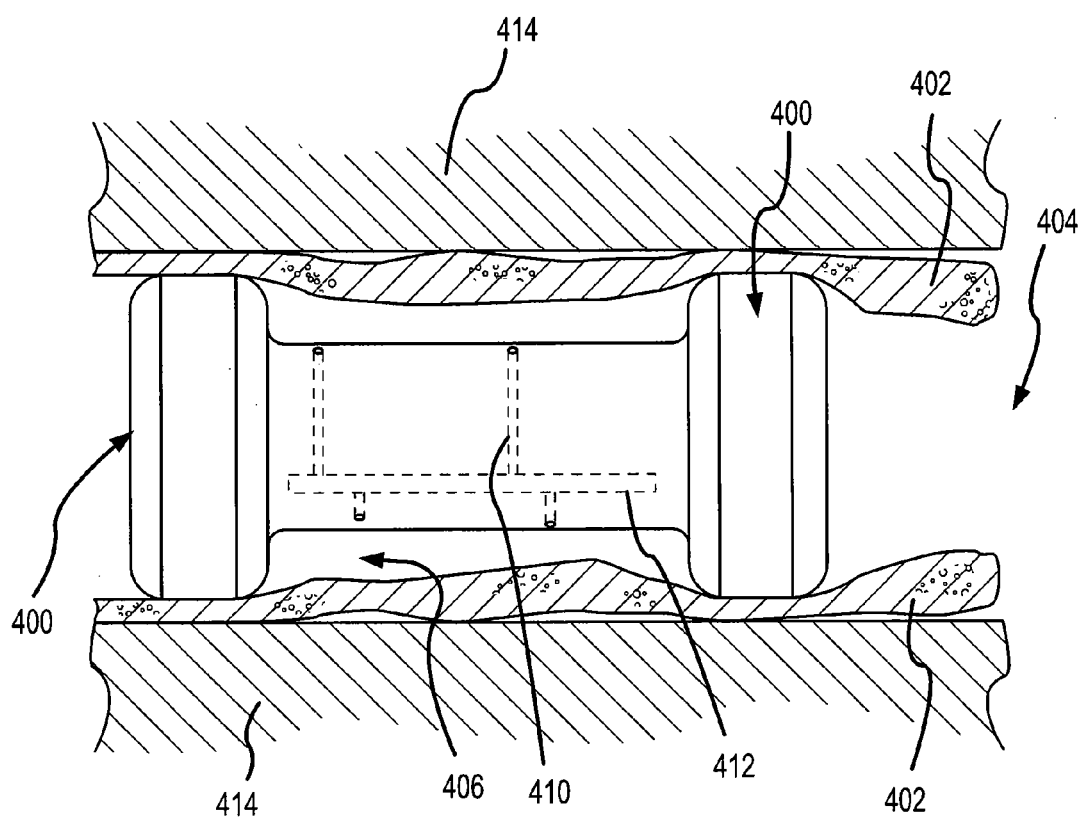
FIG. 4 shows a cross-section of another embodiment of a device installed and in a post-implantation shape with a cable member in a bone recess.

FIG. 4 shows a cross-section of another embodiment of a device 400 installed with a cable member 402 in a bone recess 404 in a bone 414. The device 400 includes an external cavity 406, a channel 410, and an internal recess 412. The external cavity 406 is connected to the channel 410. The external cavity is connected to the internal recess 412. The device may have more than one external cavity 406. The discussion of the external cavity 406 below may be applied to all shapes and shape features of a device, such as the ridges discussed above with respect to FIG. 2 (those ridges may also form at least one external cavity on a device).

The device 400 may incorporate any of the properties or elements of other devices described herein.

An external cavity 406 may be used to interact with the cable member 402 in a manner that aids the fixation of the device to the cable member and/or the fixation of the cable member to the bone recess. In one embodiment, the cavity 406 may buckle the cable member. In another embodiment, the cavity 406 may provide the cable member with an area of decreased stress, and potentially, decreased strain. The stress/strain interaction of a device, a cable member and a bone recess is described further herein.

An external cavity may hold a material (e.g., a monomer solution, a bone cement, a drug) that is useful to have held against a cable member, a bone recess or both. For example, a device 400 may allow for insertion (e.g., injection) of the material into the external cavity after the device has been installed with a cable member. In one embodiment, the device 400 allows for polymerization of a monomer liquid after the device has been installed with a cable member. In another embodiment, a device allows for insertion of a drug (e.g., a bone-growth stimulant) into the external cavity 406 after installation (e.g., for dispensing the drug over time to the bone recess and tendon).

In another embodiment, the cable member 402 may be attached to the device 400 or integrated with the device. In one embodiment, the cable member 402 may be held by a shape memory polymer of the device 400 while the device is in the post-implantation shape. For example, a cable member may contact a part of the device 400 (e.g., internal to the device, on an external wall) and the device may fixedly grip the cable member 402 while the device is in the post-implantation shape. In another embodiment, the cable member 402 may be attached via a polymerization of a solution that is in contact with the device. For example, a solution containing a linear chain and a crosslinker may be polymerized while contacting both the cable member and the device. In one embodiment, the solution contacts an external surface of the device 400. In another embodiment, the solution contacts an internal surface of the device 400. The cable member 402 also may be attached to the device 400 as described further herein.

A channel 410 may connect with an external cavity 406. For example, a channel 410 and an external recess 406 may define a contiguous volume. In one embodiment, the channel 410 is substantially cylindrical in shape, defining a shape such as a tube or pipe. In another embodiment, the channel 410 is an irregular shape. The channel 410 may connect with an internal recess 412.

The channel 410 may provide a passage for transferring a material (e.g., matter such as solids, liquids, gases) from an internal recess 412 and an external cavity 406. The channel 410 may store the material. The internal recess 412 may contain a drug or a bone cement agent. The internal recess 412 may also contain a polymerizing agent or an activation agent. The channel 410 may also contain any of these drugs or agents.

Those with skill in the art will recognize that there need not be a definite demarcation between an internal recess 406, a channel 410, and an external cavity 412, nor do those elements need to be identifiably distinct. For example, an internal recess 412 may be connected with an external cavity 406 by an orifice that defines a boundary of both the internal recess and the external cavity. In another embodiment, an orifice defines a boundary of the channel 410 and the external cavity.

An orifice may have a seal or flap restricting the transfer of matter (e.g., solids, liquids, gases) between the internal recess and the external cavity. For example, the seal (e.g., flap, orifice) may block transfers from the internal recess to the external cavity.

The seal or flap may comprise a shape memory material. In one embodiment, the seal blocks transfers of matter before the shape memory material is activated and the seal allows transfers of matter after the shape memory material is activated. In another embodiment, the seal allows transfers of matter differently before the shape memory material is activated than after the shape memory material is activated.

Activation of a shape memory material in the device may cause the internal recess to change. For example, the internal recess may be defined by a shape memory material, the activation of which changes the internal recess. In one embodiment, the activation of a shape memory material lessens the volume of an internal recess (e.g., constricts the recess). For example, the constriction of the internal recess (e.g., lessening of the volume of the recess) may deliver a drug contained in the recess to the external cavity. In another embodiment, the activation of a shape memory material expands an internal recess (e.g., increases the volume of an internal recess). For example, the expansion of the internal recess may create a low-pressure region (e.g., a partial vacuum) within the external cavity and the low-pressure region may aid in fixing the device to the cable member and/or the bone recess (e.g., through a partial vacuum in an external cavity).

In an embodiment, a selection of multiple bone implant devices having different shapes and sizes may be packaged and sold as a kit. The selection may include implants of different diameters, shapes or implants exhibiting different properties. The components within the kit may be pre-sterilized so that the kit may be opened and used during surgery without an additional sterilization step. The kit may include one or more insertion devices for inserting the implants into the bony recess as described above. Such an insertion device may include a simple metal tube shaped to engage with the one or more of the implants. Alternatively, the insertion device may be a sold shaft, a guide wire or some other component adapted facilitate insertion by the surgeon. For example, an insertion device may include a threaded rod that engages in interior threads provided by a threaded bore within the implant, which may be provided by a separate element such as a nut contained within the implant. After insertion, the rod may be unscrewed from the implant and discarded. Such an insertion device may also be used in the activation of the activation implant. For example, a stainless steel insertion rod may be heated in order to heat the implant. The kit may further include instructions for selecting the appropriate implant.

Figure 5:
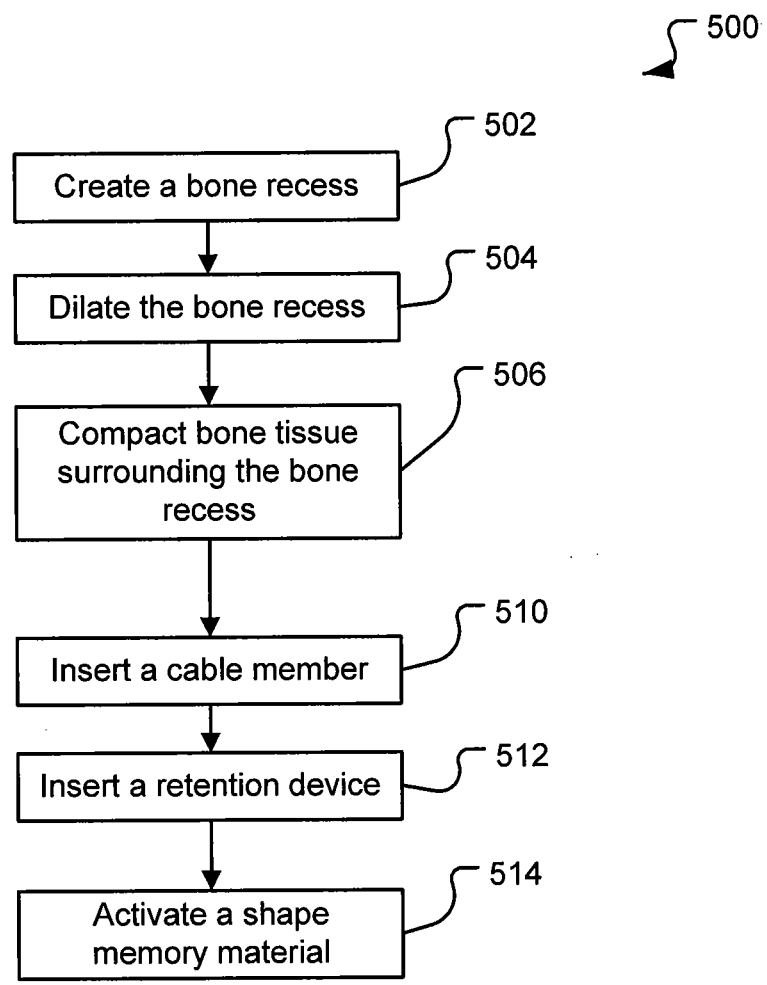
FIG. 5 shows flow-chart of a method for performing surgery.

FIG. 5 shows flow-chart of a method 500 for performing surgery. The method 500 may be embodied as a surgical procedure for repairing a joint, ligament, tendon or other anatomical part. The method 500 includes inserting a cable member 510 into a bone recess, inserting a retention device 512 into the bone recess, activating a shape memory material 514.

The method 500 may include fixing the cable member to the bone recess (not shown). In one embodiment, the method 500 performs the fixing the cable member to the bone recess operation via fixing the cable member to the retention device. In another embodiment, the method 500 performs the fixing the cable member to the bone recess operation via pinning the cable member between the retention device and a wall of the bone recess.

The method 500 includes creating a bone recess 502. Creating a bone recess 502 may be performed using techniques now known in the art (e.g., drilling), or using techniques that are yet to become known. In one embodiment, the creating a bone recess operation 502 may be adapted to create a larger surface area of bone with which a retention device may contact the bone. In another embodiment, the creating a bone recess operation 502 may be adapted to provide access to a bone site used for connecting a cable member (e.g., through the use of a retention device).

The method 500 includes dilating the recess in the bone 504. In one embodiment, the dilating the recess in the bone operation 504 is at least partially performed via compacting bone tissue surrounding the recess in the bone (e.g. 506). In another embodiment, the dilating the recess in the bone operation 504 is performed by shaving bone tissue from the walls of the bone recess.

The method 500 includes compacting bone tissue surrounding the recess in the bone 506. The compacting bone tissue operation 506 may be performed by many techniques. For example, a shape memory material in a retention device may produce sufficient pressure to compact the bone tissue surrounding a bone recess.

In one embodiment, the inserting a cable member operation 510 is performed before the inserting a retention device operation 512. For example, the cable member may be inserted 510 against a wall of the bone recess and the retention device may be inserted against the cable member and another wall (or another part of the same wall) of the bone recess. In another embodiment, the inserting of a retention device operation 512 is performed before the inserting a cable member operation 510. For example, the retention device may be inserted 512 against a wall of the bone recess (e.g., it may contact two walls, opposite sides of the same cylindrical wall, or may fill the bone recess, contacting substantially all the walls of the recess), and the cable member may be inserted 510 into the retention device. It should be noted that when the cable member is inserted 510 into the retention device, it is necessarily being inserted into the bone recess, if the retention device itself is in the bone recess.

In yet another embodiment, the inserting a cable member operation 510 and the inserting a retention device operation 512 are performed simultaneously. For example, a part of a cable member may be connected or coupled with a retention device and the combined cable member and retention device structure may be inserted into the bone recess. In one embodiment, the cable member may only be partially inserted into a bone recess. In another embodiment, the retention device may be fully inserted into a bone recess.

The method 500 may also include initiating a polymerization of a monomer solution (not shown). In one embodiment, a monomer solution is inserted into a cavity within the retention device, a cable member is inserted into the cavity, and a polymerization of the monomer solution is initiated (e.g., through heating the solution or irradiating the solution). In another embodiment, such a cavity configured for holding a monomer solution exists in the post-implantation shape of the retention device.

After the inserting a cable member operation 510 and the inserting a retention device operation 512 have been performed, the cable member and the retention device may be positioned within the bone recess in a number of configurations. Any of the configurations described herein may define the relative positions of a cable member and a retention device. For example, any of the devices in the herein description may be used as a retention device. In one embodiment, a cable member may be fixed within a cavity of the retention device. In another embodiment, a cable member may be fixed between a wall of the bone recess and an outer surface of the retention device.

In one embodiment, the inserting a retention device operation 512 may be performed by inserting one of the devices described herein comprising a shape memory material. In another embodiment, the inserting a retention device operation 512 may be performed by inserting a device separate from a shape memory material and the activating a shape memory material operation 510 may be performed on a shape memory material member separate from the device that is inserted into the bone recess.

The method 500 includes activating a shape memory material 514. The activating a shape memory material operation 510 may be performed in the manners further described herein. In one embodiment, the activating a shape memory material operation 514 may be performed by providing heat to the shape memory material. In another embodiment, the activating a shape memory material operation 514 may be performed by irradiating the shape memory material with electromagnetic radiation. The activating a shape memory material operation 514 may also be performed in manners yet to become known.

The method 500 may also include attaching sutures to the retention device and/or the cable member. In one embodiment, a suture may be attached to a part of the retention device and threaded through a part of the cable member. In another embodiment, a suture may be attached from one part of a cable member to another part of the cable member.

Figure 6:
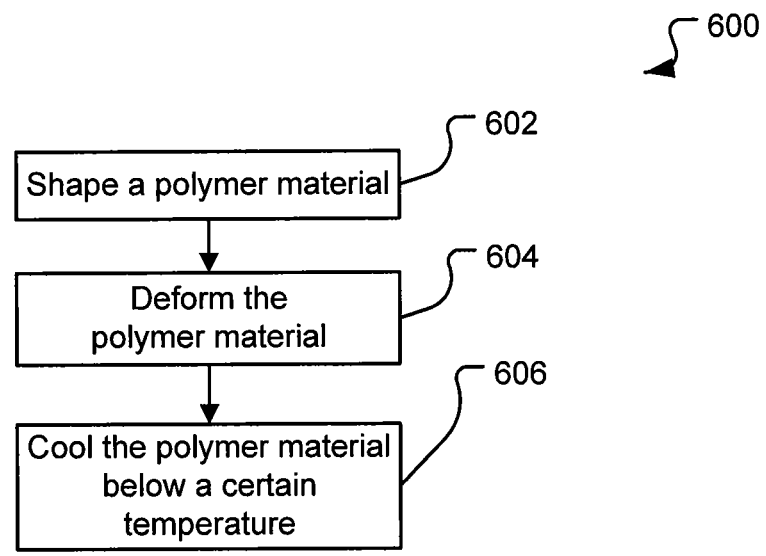
FIG. 6 shows a flow-chart of a method of manufacturing devices.

FIG. 6 shows a flow-chart of a method 600 of manufacturing devices. The method 600 includes shaping a polymer material 602 into a post-implantation shape, deforming the polymer material 604 into a pre-implantation shape, and cooling the polymer material 606 to below a certain temperature.

The method 600 includes cooling the polymer material 606 to below a certain temperature. The certain temperature may be the glass transition temperature of the polymer material. In one embodiment, the cooling the polymer material operation 606 is performed after the deforming the polymer material operation 604. For example, the polymer material may be above the glass transition temperature while the deforming the polymer material operation 604 is performed. In another embodiment, the cooling the polymer material operation 606 is performed before the deforming the polymer material operation 604.

The shaping the polymer material operation 602 may be performed in many manners. In one embodiment, the polymer material may be polymerized from a solution into a solid body while in a mold. For example, the mold may define a post-implantation shape or a pre-implantation shape. In another embodiment, the polymer material may be shaped via cutting, milling, turning (e.g., using a lathe), or other techniques used for shaping materials. As another example, the mold may hold a solution and a cable member while the solution is polymerized around an end of the cable member.

The shaping the polymer material operation 602 and the deforming the polymer material operation 604 may result in pre-implantation shapes and post-implantation shapes such as those described herein.

In another embodiment, the process 600 may include polymerizing a solution (not shown) around a cable member (e.g., while an end of a cable member is inserted in the solution). The polymerizing a solution operation may be performed to provide a strong interface between a cable member and a polymer solution. The polymerizing a solution operation may also be performed to create a device that has a cable member incorporated in the device (e.g., attached to the device, part of the device). For example, a device with an incorporated cable member may be used to facilitate surgery or to verify attachment between the device and cable member before a surgical procedure is begun. The incorporation of a cable member in a device is further described herein in relation to other devices and methods.

Polyethylene glycol dimethacrylate-poly methyl methacrylate (PEGDMA-PMMA) compositions and polyethylene glycol-poly methyl methacrylate (PEG-PMMA) are described herein as examples of SMPs that may be used for devices. PEGDMA-PMMA and PEG-PMMA are described herein partially because of the biocompatability of the substances and the high forces the substances are often able to generate. PEGDMA may be referred to as PEG for short, although PEG may mean other functionalized forms of polyethylene glycol.

By combining PEG with a functional group (e.g, DMA) into novel SMP compositions, a range of glass transition temperatures and installment forces (e.g., post-implantation forces creating pressures on bone recesses) may be selected. In some instances, the glass transition temperature of a SMP composition will vary with (or otherwise be related to) the installment force achievable by the SMP. By utilizing two or more different cross-linkers, the relationship between the glass transition temperature of a SMP and the installment force achievable by the SMP may be varied or even non-associated (e.g., the Tg and installment force may be varied independently).

The percentage (as a function of total weight of the polymer, or by weight) of cross-linker in the polymer composition may also be varied. The amount of cross-linker in a polymer composition may be varied to change the polymer compositions characteristics (e.g., strength, force, glass transition temperature, response time, elasticity). In one embodiment, a cross-linker may comprise about 5% or less of a polymer composition. In another embodiment, a cross-linker may comprise more than about 10% of a polymer composition. In yet another embodiment, a cross-linker may comprise about 80% of a polymer composition.

The following examples describe some of the experimental results achieved with respect to creating SMPs with various glass transition temperatures and installment forces.

EXAMPLES

Experimental work on SMP systems used in graft fixation devices was performed to demonstrate the feasibility and advantages of these devices over currently used ACL fixation devices.

The following examples are presented to demonstrate a SMP polymerization process, fabrication, characterization and testing of materials in accordance with the present invention. These examples are not intended to limit the scope of the invention in any way. All starting materials are commercially available. Thermomechanical characterization was performed by dynamic mechanical analysis (DMA) on a Perkin Elmer Dynamic Mechanical Analyzer DMA-7.

Example 1

SMP Fabrication

A tert-butyl acrylate (tBA) monomer (Aldrich), poly (ethyleneglycol) dimethacrylate (PEGDMA) cross-linker (Aldrich), and the photoinitiator 2,2-dimethoxy-2-phenylacetophenone (Aldrich) were used in their as-received condition without further purification. A polymer solution was formulated by combining 10 wt % PEGDMA, 0.1 wt % initiator, with the balance tBA. Other crosslinker/monomer ratios can be considered and can range from 1 wt %-99 wt % cross-linker. Other photoinitiators include acetophenone, anisoin, anthraquinone, benzene chromium tricarbonyl, benzil, benzoin, benzoin ethyl ether, benzoin isobutyl ether, benzoin methyl ether, benzophenone, 4-benzoylbiphenyl, 2-benzyl-2-(dimethylamino)-4'-morpholinobutyrophenone, 4,4'-bis(diethylamino)-4'benzophenone, 4,4'-bis(dimethylamino)-4'benzophenone, camphorquinone, 2-chlorothioxanthen-9-one, dibenzosuberenone, 2,2-diethoxyacetophenone, 4,4'-dihydroxybenzophenone, 4-(dimethylamino)benzophenone, 4,4'-dimethylbenzil, 2,4(5)'-dimethylbenzophenone, 3,4-dimethylbenzophenone, 4'-ethoxyacetophenone, 2-ethylanthraquinone, ferrocene, 3(4)'-hydroxyacetophenone, 3(4)'-hydroxybenzophenone, 1-hydroxycyclohexyl phenyl ketone, 2-hydroxy-2-methylpropiophenone, 2(3)-methylbenzophenone, methyl benzoylformate, 2-methyl-4'-(methylthio)-2-morpholinopropiophenone, phenanthrenequinone, 4'phenoxyacetophenone, thioxanthen-9-one, triarylsulfonium hexafluoroantimonate salts, and triarylsulfonium hexafluorophosphate salts.

Glass slides, approximately 1"×3"×1 mm, were pre-coated with a hydrophobic polymer glass treatment solution (RainX glass treatment sold by SOPUS Products, Houston, Tex.), which acted as a non-reactive releasing agent. The glass slides were separated with 1 mm spacers. The above solution was mixed manually in a glass vial and then injected between two glass slides using a pipette. Photopolymerization was then achieved by placing the solutions under a UV lamp (Model B100AP, UVP Blak-Ray) at an intensity of ~10 mW/cm$^2$ for 10 minutes. Samples for thermomechanical testing were laser cut from the polymer to dimensions of 20 mm×5 mm×1 mm. The edges of the samples were polished using 600-grit silicon carbide sandpaper to remove any edge effects caused by the laser cutting. The material was stored in a refrigerator with no light contact.

SMP's may be photopolymerized in a semi-UV transparent mold. This includes polymerization through glass molds, such as test tubes or custom shaped glassware, silicone molds, or any degradable mold, such as water-soluble molds. Thermal initiation can be used in place of phoyopolymerization. With thermal initiation, the initiator reacts to heat instead of UV light. Benzoyl-peroxide and other thermal initiators can be used. In this case, any removable mold may be used in molding SMP devices. Other methods of machining include CNC machining for complex geometries and lathing for cylindrical specimens.

Storage and stability of the polymer were tested in two ways. First, a packaged plug was stored in a freezer for ~1 year under no constraint. The plug was then heated in a body temperature bath and the plug recovered to its original shape (e.g., unconstrained shape, pre-deformed shape). Second, samples were placed in a body temperature saline bath (pH=7.4) for 6 months. Weight measurements (to determine if any hydrolytic degradation had occurred) were taken every 2-4 weeks. The polymer showed no signs of weight loss or degradation after 6 months.

Example 2

SMP Thermomechanical Characterization

The polymer samples were tested using a Perkin Elmer Dynamic Mechanical Analyzer (DMA-7). A three-point flexural configuration was used for glass transition ($T_g$), strain recovery, and stress recovery tests (FIG. 24 inset). The three-point flexure loading allowed reasonable stress/strain levels in the sample for the temperature range spanning the glassy to the rubbery state. In particular, this configuration allowed 30% maximum bending strain over a 5 mm span during the stress and strain recovery tests. FIG. 24 shows a comparison between the PEGDMA copolymer and PLA, which is a biodegradable polymer used in tibial devices. The drop in storage modulus as temperature increases indicates the material is transforming from a glassy or stiff state to a rubbery state. Also, $T_g$ may be defined in relation to the peak of the tan delta curve.

The glassy storage modulus is an indication of the material's stiffness. A SMP plug will have a stiffness close to PLA after installation. Furthermore, PLA will show some minor shape memory effect around its glass transition. It may then be possible to engineer the PLA system to exhibit a large shape memory effect. The material selected for this study is not the only choice. It may be possible, with the correct polymer engineering, to match the necessary material characteristic to current FDA approved polymer devices.

The test results shown in FIG. 24 may offer insight into the thermomechanics of shape-storage deformation and shape recovery of SMPs. A three-point flexural configuration (shown in FIG. 24) may be used for glass transition, free strain recovery, and stress recovery tests. In all tests, heating and cooling is typically performed at a constant rate of 5° C./min with data collection every 2 seconds. For example, in Tg tests, samples were cycled at a frequency of 1 Hz between minimum and maximum bending forces of 10 mN and 90 mN. The glass transition temperature (Tg) of the polymers was tested over a range of 100° C. and depended on the molecular weight and concentration of the crosslinker. The polymers showed a 100% strain recovery up to maximum strains of approximately 80% at low and high deformation temperatures (Td). Free strain recovery depended on the temperature during deformation. For example, lower deformation temperatures (Td<Tg) decreased the temperature required for free strain recovery. Constrained stress recovery shows a complex evolution as a function of temperature and also depends on Td. In an embodiment, using variations of crosslinking density, nano reinforcement, fiber reinforcement, the amount of deformation (e.g., the ratio of compression, the ratio of expansion), or layering, a SMP may withstand a range from 0.5 MPa to 20 MPa stress levels. Tendon slippage is unlikely to occur with installed fixation loads above about 0.25 MPa.

Example 3

Plug Manufacturing

The test plug material was machined from a 45 wt % PEGDMA ratio to 55% PMMA (poly methyl methacrylate) with a 0.1% photo initiator and mixed in a 14 mm diameter glass test tube. The open end of the test tube was blocked off with a rubber stopper and the test tube plus solution was placed in a 0° C. water bath under a UV lamp for 10 minutes. The glass test tube was then removed leaving a 14 mm PEGPMMA cylinder with a glass transition temperature ($T_g$) of 40° C. The plugs were machined from the cylinder stock using coconut oil as lubricant and spinal speeds of 450 RPM to be approximately 11.5 mm in diameter and 25.4 mm in length. The edges of the device were filleted to 0.5 mm radii to ensure the device would not shear a soft tissue (tendon) on contact.

In addition, various unconstrained (or un-deformed) shapes were created to demonstrate multiple forms of possible unconstrained shapes, shown in FIG. 7. Unconstrained shapes and their differences from post-implantation shapes are described further herein.

Figure 8:
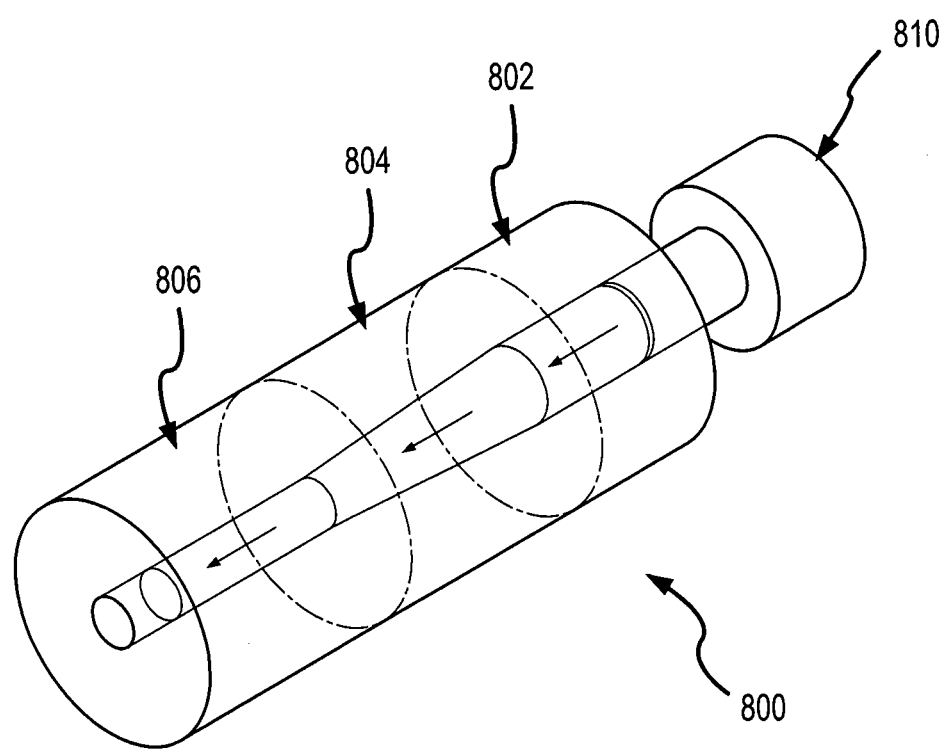
FIG. 8 shows a polymer extrusion unit.
Figure 9A:
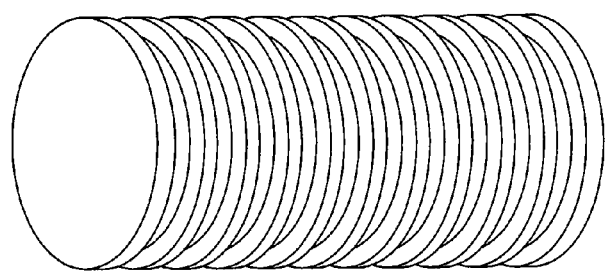
FIG. 9a shows an embodiment of a pre-deformed or unconstrained shape.
Figure 9B:
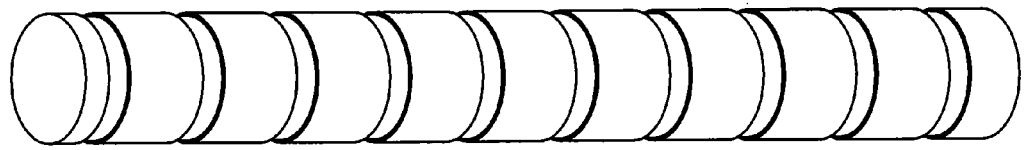
FIG. 9b shows and embodiment of a deformed shape or pre-implantation shape.

The plugs were then coated with lubricant (e.g., spray Teflon) and prepared for insertion in an extrusion apparatus. The extrusion apparatus deforms plugs into a deformed shape, for example, into a pre-implantation shape. FIG. 8 shows the three extrusion stages that the SMP undergoes in the current setup. The extrusion unit 800 operates by placing the un-deformed plug in an entry zone 802 in the extrusion unit 800 and applying a pressure using a hardened pressure bar 810 to push the plug into the reduction zone 804. An additional plug (or dummy plug) may be inserted to transmit a force onto the plug in the reduction zone 804 and further deform the plug to conform with the final zone 806 (e.g., the plug being then in a pre-implantation shape). After the polymer has been fully extruded into the final dimension zone, the extrusion unit is placed in a controlled temperature environment below the polymers glass transition, to allow the polymer to set in its temporarily deformed stored shape. The polymer may then be released at room temperature or below (depending on the Tg of the polymer). FIGS. 9a and 9b, show the pre-deformed shape (the original shape or unconstrained shape) and the deformed shape (pre-implantation shape). Storing the deformed plug at a temperature below its glass transition temperature can reduce incidence of premature deployment (e.g., expansion to post-implantation shape or unconstrained shape depending on constraints present during deployment).

Figure 10:
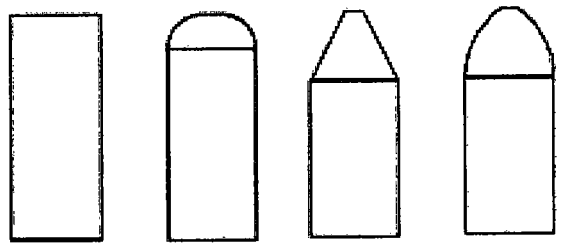
FIG. 10 shows different tip geometries of devices.

The geometry and material mechanics were varied during experimentation. FIG. 10 shows different tip geometries of devices used during the installation process to analyze the effect of device insertion force as a function of geometry. The experimental results indicated devices with the more tapered or "aerodynamic" appearing configurations provided the easiest insertion into bone recesses.

Figure 11:
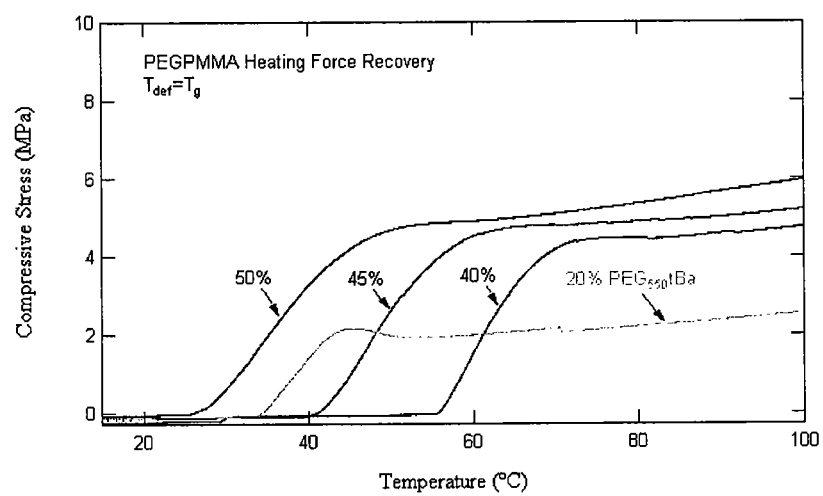
FIG. 11 shows experimental results of stresses of several polymer compositions.
Figure 12:
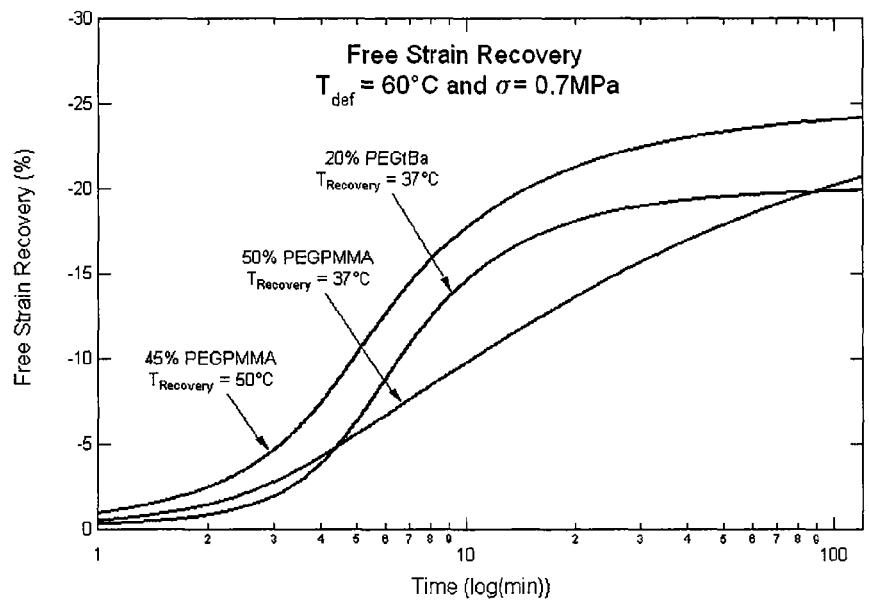
FIG. 12 shows the free strain recovery time of devices strained and then stored in the strained state before recovery was initiated.
Figure 13:
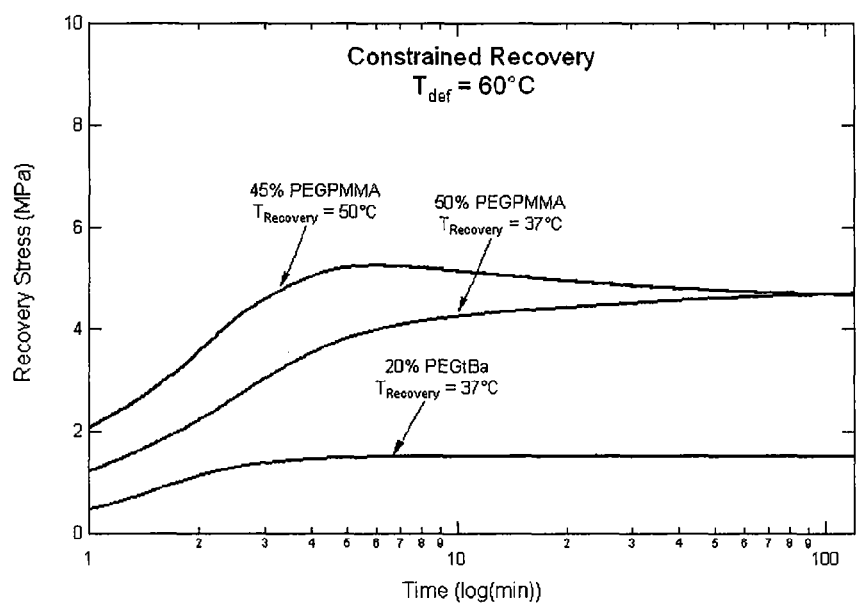
FIG. 13 shows experimental results of constrained recovery time as a function of crosslinking.

Several different polymers compositions were used to vary the recovery force of the SMP, for example the 20 wt % PEG to tBa system shows a lower recovery force than the 40, 45, 50 wt % PEG to PMMA compositions, FIG. 11. This allows for the recovery force of the polymer to be varied with regards to linear chain material and percent crosslinking. The variation in percent crosslinker also affected the glass transition and allowed the polymer to recover at different temperatures. FIG. 12 shows the free strain recovery time after devices (e.g., SMP plugs) were strained (e.g., deformed) between about 25% and about 30% then stored in the strained state before recovery was initiated. The $T_{recovery}$ (e.g., recovery temperature) indicated in the figure references the transition temperature of the device. FIG. 13 shows constrained recovery time as a function of crosslinking.

After performing the above experiments, plugs were created to have a 45 wt % PEG PMMA composition with the crosslinker having a molecular weight of 875. This allowed for the optimal deployment temperature to be body temperature. The deployment temperature can be raised or lowered by changing the material composition. Changing material composition will also influence the deployment time and force after activation.

Example 4

Recovery Force

Figure 14:
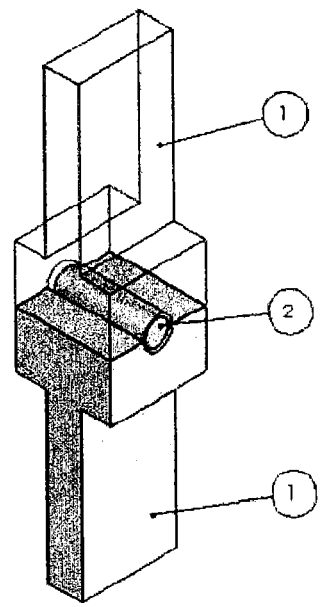
FIG. 14 shows a custom force measuring fixture.
Figure 15:
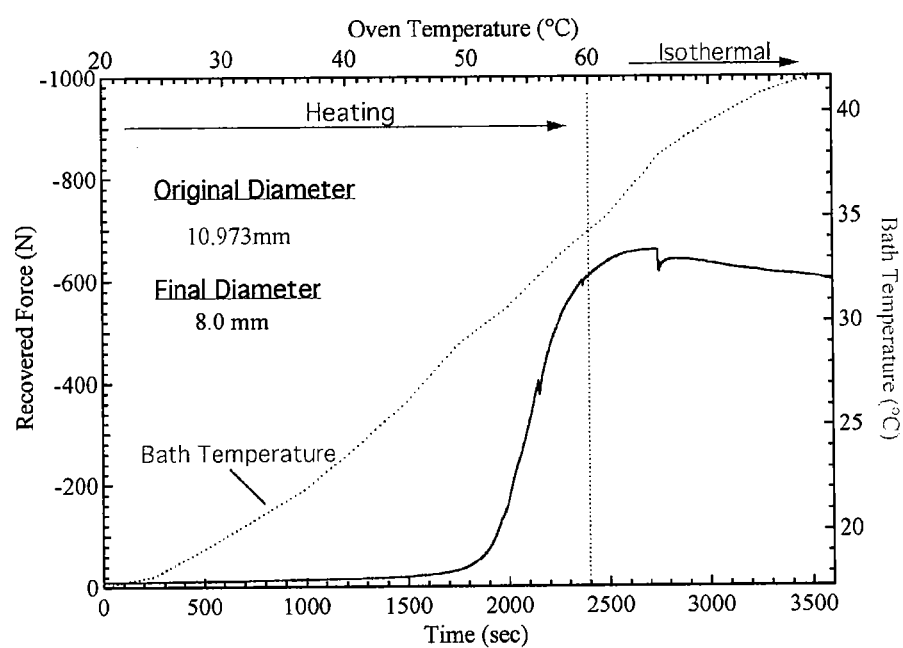
FIG. 15 shows experimental results of the recovery load of a shape memory polymer plug.

Two forms of testing have been designed to compare the utility of the current interference screw to utility of a SMP fixation device (e.g., a SMP plug). The first test analyzed the force caused from the recovery of a 20 wt % PEG tBa SMP plug when confined in a 10 mm tunnel with tendon. To simulate the boney tunnel, the custom fixture (FIG. 14) was manufactured from aluminum and mounted inside a thermally controlled chamber. The plug (2) in its deformed position was placed between aluminum constraints (1) and the extension fixed. The temperature was increased gradually over time and the SMP plug recovered gradually resulting in a compressive loading being applied to the aluminum fixture (FIG. 14). It should be noted that the SMP plug recovered via contracting some of the plug's dimensions and expanding some of the plug's dimensions. The results, FIG. 15, show the recovery load of an 11 mm diameter SMP plug is approximately 600N. This force is arbitrary and can be increased or decreased by, for example, changing the dimensions of the SMP plug (e.g., in the unconstrained shape or original shape) or changing the composition of the SMP (e.g., changing the type or percentage of cross-linker). This is because the recovery force is dependant on the geometry and composition of the plug, which can be changed during the manufacturing process.

Figure 16:
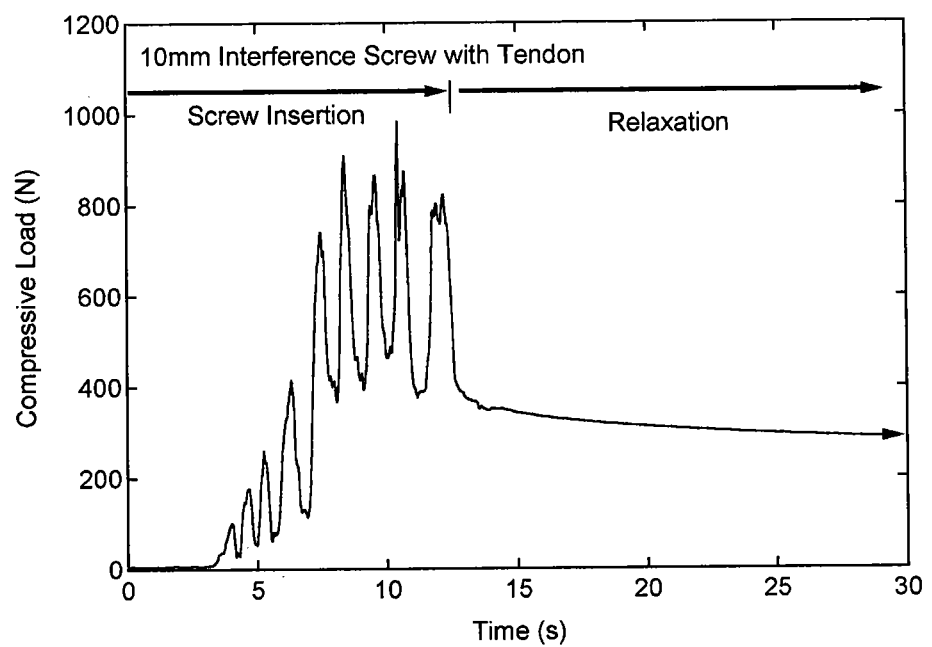
FIG. 16 shows experimental results of the load of a prior art interference screw.

The second test, FIG. 16, measured the forces for the prior art interference screw during insertion and after insertion. This was achieved by recording the force exerted on a 10 mm constrained tunnel (e.g., through the fixture in FIG. 14) during insertion of a 10 mm interference screw. FIG. 16 shows the immediate increase and relaxation in the force levels (e.g., loads) during the installation of the interference screw and a gradual relaxation of the device and tendon construct post-installation. The spiking and relaxation of the loads in the interference screw are directly related to an application of a variable torque to the device used to install the screws.

Example 5

Failure Strength

Figure 17:
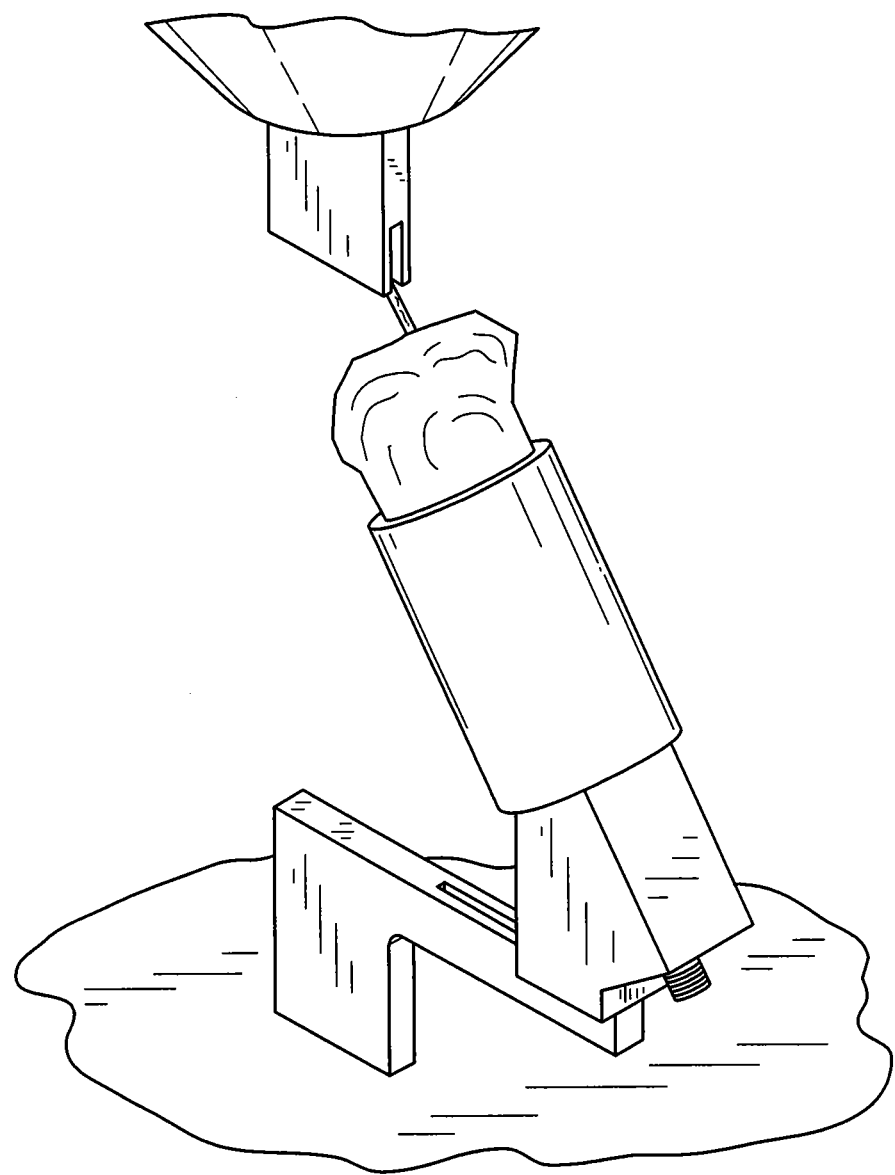
FIG. 17 shows a test setup for an in-vitro maximum failure strength and cyclic strength of a fixation device as installed.

FIG. 17 shows the test setup for the in-vitro maximum failure strength and cyclic strength of the ACL tendon construct. Three hundred bovine knees were harvested and cleaned of soft tissue. 100 bovine extensor tendons were also harvested. The bone mineral density of the specimens ranged from 0.78 g/cm$^3$ to 0.84 g/cm$^3$, thus closely approximating the bone mineral density of young human tibia.

The bone was mounted into a custom made fixture (FIG. 17), which provided access to the distal opening of the tibial tunnel. A 10-mm diameter tibial tunnel was drilled from the anteromedial proximal metaphysis to the mid-articular surface of the proximal tibia with the aid of a standard ACL tibial guide set to fifty-five degrees. A four-stranded, non-weaved cable member (e.g., graft) was prepared by passing tendons (10 mm sized) over doubled number 1 absorbable sutures. Each end of the four-stranded graft was secured with a running, interlocking, whip stitch using #1 fiberwire in order to apply tension to each limb of the graft during fixation. Unfortunately, due to the in-vitro deployment simulation requirements of the SMP plug, this initial pretension force was lost. After the soft tissue graft was passed retrograde through the 10 mm tibial tunnel, a 4 mm stainless steel rod was passed through the looped end of the graft and attached to the upper cross head of a screw driven uniaxial testing machine, representing the femoral fixation site. The SMP plug was then inserted in its deformed position to the approximate center of the tendon construct as shown in FIG. 17. The entire specimen was removed and placed in body temperature saline for 30 minutes to initiate shape memory recovery. The specimen was then placed back into the custom fixture. Using extension control the crosshead was run at 0.25 mm/sec until a displacement of 30 mm had been reached.

The shape memory polymer material selected for these plugs was 45 wt % PEGDMA to PMMA and manufactured to have an initial deployed diameter of 11.5 mm and a length of 25.4 mm. The plugs were then deformed using a extrusion unit (e.g., extrusion device described in example 3) to a final diameter of 8 mm. The deformed plugs were stored at 0° C. in a glass vial until 5 min prior to installation. The glass plugs were then inserted using a 10 mm diameter, 3 inch long cylindrical shaped push rod used to insert the plug into position.

Figure 18:
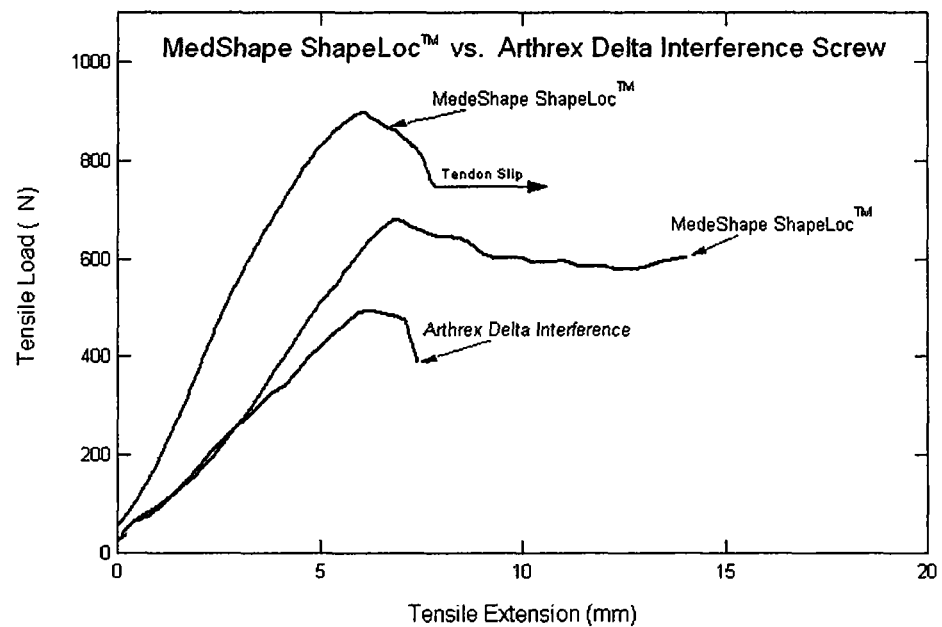
FIG. 18 shows experimental results comparing SMP fixation devices and a Delta Interference Screw.
Figure 19:
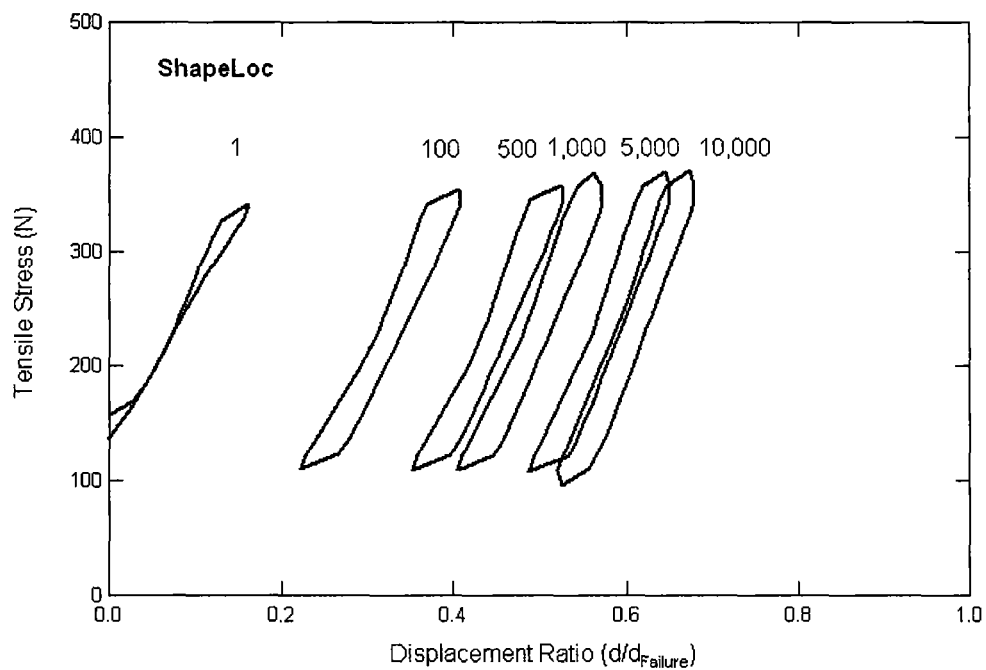
FIG. 19 shows experimental results comparing tensile strengths and displacement ratios of the cyclic response (e.g., response to multiple cycles) of a ShapeLoc fixation device.

FIG. 18 shows experimental results comparing SMP fixation devices (ShapeLoc devices by MedShape Solutions, Inc., Castle Rock, Colo.) and a Delta Interference Screw (by Arthrex, Inc., Naples, Fla.). FIG. 19 shows experimental results comparing tensile strengths and displacement ratios of the cyclic response (e.g., response to multiple cycles) of a ShapeLoc fixation device. FIG. 20a shows mean and standard deviations of tensile strengths of various fixation devices. FIG. 20b shows mean and standard deviations of stiffnesses of various fixation options. FIG. 20c shows mean and standard deviations of slip rates of various fixation options.

Example 6

Tissue Incorporation

A photo-polymerization process allows for a cable member (e.g., a synthetic graft, a living tissue) to be encapsulated within a polymer material. In one embodiment, the encapsulation provides a more complete interface, thus reducing the incidence of a cable member (e.g., a tendon) slipping or tendon-device damage. In another embodiment, the encapsulation provides an interface that may be tested before installation in a surgery site.

The use of the PEGDMA-PMMA system allows for strong adhesion between the tendon and the device. This allows the graft to be directly attached (e.g., polymerized) to the fixation device.

Figure 21:
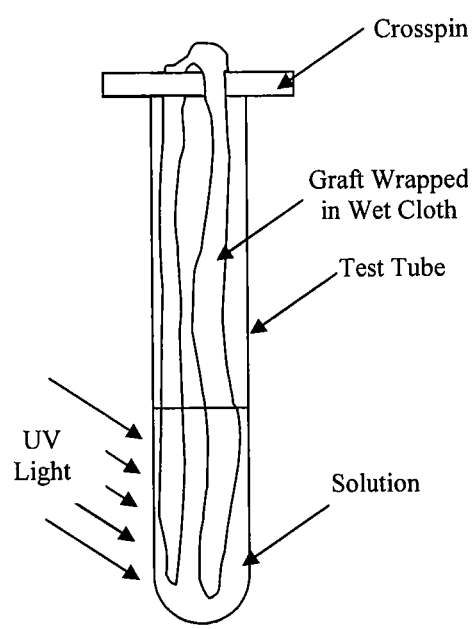
FIG. 21 shows a tissue encapsulation setup.

The shape memory polymer system used for this example was the 45 wt % PEG to PMMA and prepared similar to example 1. FIG. 21, shows a tissue encapsulation setup and is described below. The tendon was sized to be inserted into a 10 mm tunnel. The tendon was carefully wrapped in a cold saline soaked cloth leaving only a 25 mm portion of the tendons distal end exposed. A 12 mm glass test tube was then coated with a hydrophobic polymer glass treatment solution (RainX glass treatment sold by SOPUS Products, Houston, Tex.) and the SMP solution was poured into the base of the tube. The tendon, leading with the uncovered end was lowered into the polymer solution until the upper looped portion was restricted with a crosspin. The distal tendon ends were pressed against a wall of the test tube. The setup, shown in FIG. 21, was then placed under the direct contact from a UV lamp and was slowly rotated over a course of 10 minutes until full polymerization had occurred. The combined tendon and polymer device was then removed from the glass tube and stored in a household freezer.

This example represents the idea of incorporating the tendon directly to the device prior to surgical installation. Example 7 will illustrate the use of the device to provide a barrier to allow the tendon and SMP plug to be installed within the bone tunnel, followed by a monomer solution being polymerized inside the tunnel.

Example 7

Tissue Incorporation

Figure 22C:
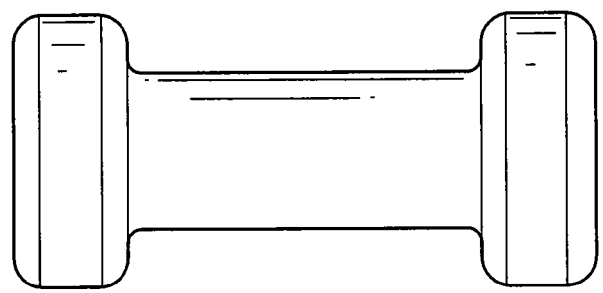
FIG. 22C shows a device in an unconstrained shape.
Figure 22B:
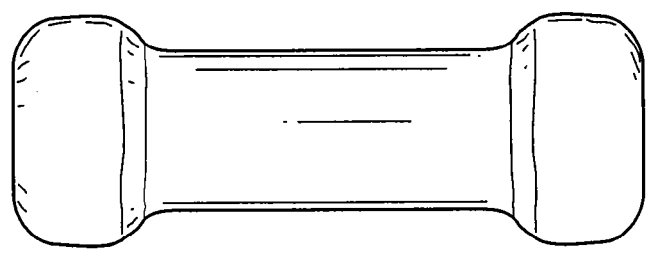
FIG. 22B shows a device in a mid-deployment shape.
Figure 22A:
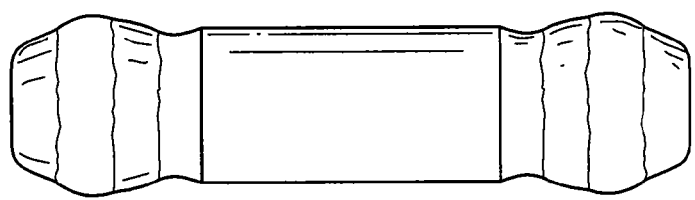
FIG. 22A shows a device in a pre-implantation shape.
Figure 23:
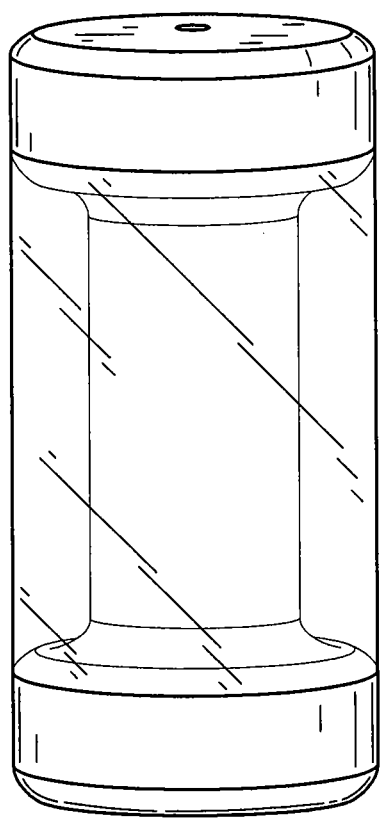
FIG. 23 shows a device with a polymerized solution around the device.

In this experiment a SMP device was machined (e.g., lathed) from 45 wt % PEG to PMMA to resemble a "dog bone" type shape. The two ends were deformed at 60° C., as shown in FIG. 22a, and stored at 0° C. The deformed SMP plug was inserted with a 10 mm sized tendon into a 10 mm foam bone tunnel (used to model human bone). The foam, tendon and deformed device (e.g., device in its pre-implantation shape) was then placed in body temperature saline and heated for 10 minutes. FIGS. 22a-c show the device during the device's change from a pre-implantation shape (FIG. 22a) through a mid-deployment shape (FIG. 22b), toward the device's unconstrained shape (FIG. 22c). After the device showed near full change to the post-implantation shape (as installed) an 18G syringe was used to deposit a mixture of 45 wt % PEG to PMMA solution with 0.1% photo-initiator. Next an ultraviolet light source was located at the open end of the tunnel and initiated the free radical polymerization through the SMP device of the solution (45 wt % PEG to PMMA solution with 0.1% photo-initiator) distributed around the device (FIG. 23).

There are two reasons for using a SMP device in this example. The first reason is to ensure the maximum amount of the soft tissue comes into the contact with the bone tunnel wall. This will aid the healing and tendon regeneration process. The second reason is to allow a barrier to restrict the use of the PEG-PMMA mixture to only the boney tunnel. An additional method is the use of a thermal initiator with an activation temperature at body temperature. This would allow the initial SMP plug to hold the tendon in place while the remaining PEG-PMMA solution (or even a homomonomer of PMMA) polymerizes over time due to the heat energy generated from body temperature.

While various embodiments have been described for purposes of this specification, various changes and modifications may be made which will readily suggest themselves to those skilled in the art and which are encompassed in the spirit of the invention both disclosed herein and as defined in the appended claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

What is claimed is:

1. An amorphous polymerized composition comprising
a linear chain comprising tert-butyl acrylate; and
a first cross-linker comprising polyethylene glycol dimethacrylate; wherein
the amorphous polymerized composition exhibits a glass transition at a temperature between about 34° C. and about 50° C., inclusive;
the amorphous polymerized composition comprises 5% to 80% by weight of the polyethylene glycol dimethacrylate; and
the amorphous polymerized composition exhibits shape memory effects.

2. The amorphous polymerized composition of claim 1 further comprising a photoinitiator.

3. The amorphous polymerized composition of claim 1 comprising more than about 10% by weight of the polyethylene glycol dimethacrylate.

4. The amorphous polymerized composition of claim 1, wherein the shape memory polymer comprises 20% by weight of polyethylene glycol dimethacrylate.

5. The amorphous polymerized composition of claim 1, wherein the glass transition temperature is about 37° C.

6. The amorphous polymerized composition of claim 2, wherein the photoinitiator comprises 2,2-dimethoxy-2-phenylacetophen one.

7. The amorphous polymerized composition of claim 1, wherein a recovery time of the amorphous polymerized composition is between 10 seconds and 10 minutes.

8. A device for in vivo medical applications comprising
a chemically-cross-linked, shape memory polymer comprising
tert-butyl acrylate as a first monomer; and
polyethylene glycol dimethacrylate as a second chemically crosslinking monomer; wherein
the shape memory polymer comprises 5% to 80% by weight of polyethylene glycol dimethacrylate;
the shape memory polymer has a glass transition temperature between about 34° C. and 50° C., inclusive;
the device is formed of the shape memory polymer in an original shape;
the device is deformed from the original shape for use in the in vivo medical application; and
the device recovers to the original shape upon being placed in vivo at body temperature.

9. The device of claim 7, wherein the shape memory polymer comprises 20% by weight of polyethylene glycol dimethacrylate.

10. The device of claim 7 further comprising a photoinitiator.

11. The device of claim 10, wherein the photoinitiator is 2,2-dimethoxy-2-phenylacetophenone.

12. The device of claim 7, wherein the shape memory polymer has a glass transition temperature of about 37° C.

13. The device of claim 7, wherein the shape memory polymer an elastic modulus between 0.5 MPa and 20 MPa, inclusive.

14. The device of claim 7, wherein a recovery time of the shape memory polymer is between 10 seconds and 10 minutes.

15. The device of claim 7, wherein recovery time of transformation of the shape memory polymer is a function of a deformation temperature ($T_d$).

16. The device of claim 7, wherein the shape memory polymer further comprises a hydrogel material.

17. The device of claim 14, wherein
   the recovery time is a function of an amount of the polyethylene glycol dimethacrylate in the shape memory polymer.

18. The device of claim 7, wherein selection of an amount of polyethylene glycol dimethacrylate changes the glass transition temperature.

* * * * *